(12) United States Patent
Mattson et al.

(10) Patent No.: US 7,462,700 B2
(45) Date of Patent: Dec. 9, 2008

(54) CANINE RANKL AND METHODS FOR PREPARING AND USING THE SAME

(75) Inventors: Jeanine D. Mattson, San Francisco, CA (US); Terrill McClanahan, Sunnyvale, CA (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 369 days.

(21) Appl. No.: 10/537,864

(22) PCT Filed: Dec. 10, 2003

(86) PCT No.: PCT/US03/39292

§ 371 (c)(1),
(2), (4) Date: Jun. 7, 2005

(87) PCT Pub. No.: WO2004/052233

PCT Pub. Date: Jun. 24, 2004

(65) Prior Publication Data

US 2006/0154858 A1 Jul. 13, 2006

Related U.S. Application Data

(60) Provisional application No. 60/432,092, filed on Dec. 10, 2002.

(51) Int. Cl.
*C07K 14/51* (2006.01)
*C07K 14/00* (2006.01)
*C12N 5/00* (2006.01)
*C12N 15/00* (2006.01)
*A61K 38/00* (2006.01)

(52) U.S. Cl. .............. 530/399; 530/350; 435/69.1; 435/320.1; 435/325; 536/23.4; 536/24.1

(58) Field of Classification Search .............. None
See application file for complete search history.

(56) References Cited

U.S. PATENT DOCUMENTS

| | | | |
|---|---|---|---|
| 5,843,678 A | 12/1998 | Boyle | |
| 6,017,729 A * | 1/2000 | Anderson et al. | 435/69.1 |
| 6,242,213 B1 | 6/2001 | Anderson | |
| 6,242,586 B1 | 6/2001 | Gorman et al. | |
| 6,316,408 B1 * | 11/2001 | Boyle | 514/12 |
| 6,419,929 B1 | 7/2002 | Anderson | |
| 6,525,180 B1 | 2/2003 | Gorman et al. | |
| 6,645,500 B1 | 11/2003 | Halkier et al. | |
| 6,838,262 B1 * | 1/2005 | Anderson et al. | 435/69.7 |
| 7,192,718 B2 | 3/2007 | Yamaguchi et al. | |
| 2002/0081720 A1 | 6/2002 | Dougall et al. | |
| 2002/0086826 A1 | 7/2002 | Anderson et al. | |
| 2002/0086827 A1 | 7/2002 | Anderson | |
| 2002/0169117 A1 | 11/2002 | Maraskovsky | |
| 2003/0175840 A1 | 9/2003 | Anderson et al. | |
| 2003/0176647 A1 | 9/2003 | Yamaguchi et al. | |
| 2003/0198640 A1 | 10/2003 | Yu et al. | |
| 2003/0208045 A1 | 11/2003 | Yamaguchi et al. | |
| 2005/0003391 A1 | 1/2005 | Anderson | |
| 2005/0003457 A1 | 1/2005 | Yamaguchi et al. | |
| 2005/0147611 A1 | 7/2005 | Boyle et al. | |
| 2005/0208580 A1 | 9/2005 | Yamaguchi et al. | |
| 2007/0009520 A1 | 1/2007 | Yamaguchi et al. | |

FOREIGN PATENT DOCUMENTS

| | | |
|---|---|---|
| WO | WO 96/14328 | 5/1996 |
| WO | WO 97/23614 | 7/1997 |
| WO | WO 98/25958 | 6/1998 |
| WO | WO 98/28424 | 7/1998 |
| WO | WO 98/28426 | 7/1998 |
| WO | WO 98/46751 | 10/1998 |
| WO | WO 00/08139 | 2/2000 |
| WO | WO 00/15807 A1 | 3/2000 |
| WO | WO 01/03719 A2 | 1/2001 |
| WO | WO 01/23549 A1 | 4/2001 |
| WO | WO 02/04643 A1 | 1/2002 |

OTHER PUBLICATIONS

Anderson et al., "A homologue of the TNF receptor and its ligand enhance T-cell growth and dendritic-cell function" *Nature*, 390(6656):175-179 (1997).

Bax et al., "Stimulation of osteoclastic bone resorption by hydrogen peroxide", *Biochemical and Biophysical Research Communications*, 183(3):1153-1158 (1992).

Bertolini et al., "Stimulation of bone resorption and inhibition of bone formation in vitro by human tumour necrosis factors", *Nature*, 319:516-518 (1986).

Bolin et al., "HNMP-1: A Novel Hematopoietic and Neural Membrane Protein Differentially Regulated in Neural Development and Injury", *The Journal of Neuroscience*, 17(14):5493-5502 (1997).

Chambers, T. J., "Regulation of the differentiation and function of osteoclasts", *Journal of Pathology*, 192(1):4-13 (2000).

Collin et al., "Constitutive expression of osteoclast-stimulating activity by normal clonal osteoblast-like cells: effects of parathyroid hormone and 1,25-dihydroxyvitamin D3" *Endocrinology*, 131(3):1181-1187 (1992).

Cunningham et al., "Receptor and Antibody Epitopes in Human Growth Hormone Identified by Homolog-Scanning Mutagenesis" *Science*, 243:1330-1336 (1989).

Hall et al., "The Role of Reactive Oxygen Intermediates in Osteoclastic Bone Resorption", *Biochemical and Biophysical Research Communications*, 207(1):280-287 (1995).

(Continued)

*Primary Examiner*—Marianne P. Allen
*Assistant Examiner*—Regina M DeBerry

(57) ABSTRACT

The present invention provides isolated nucleic acid molecules that encode a substantial part of canine RANKL polypeptide, including the extracellular domains of that polypeptide, the polypeptide and fragments thereof. Vectors and host cells encoding and expressing canine RANKL polypeptide are provided, as well as antibodies that bind to RANKL and that inhibit RANKL activity. Also provided are methods of treating an animal to inhibit or treat the loss of bone minerals.

22 Claims, No Drawings

OTHER PUBLICATIONS

Hughes et al., "Genetic linkage of familial expansile osteolysis to chromosome 18q", *Hum. Mol. Genet.*, 3(2):359-361 (1994).

Jimi et al., "Osteoclast function is activated by osteoblastic cells through a mechanism involving cell-to-cell contact", *Endocrinology*, 137(5):2187-2190 (1996).

Kearns et al., "RANKL and OPG Regulation of Bone Remodeling in Health and Disease", *Endocr. Rev.*, pp. 1-84; Rapid Electronic Publication first published on Dec. 5, 2007 as doi:10.1210/cr.2007-0014.

Khosla, S., "Minireview: The OPG/RANKL/RANK System", *Endocrinology*, 142(12): 50505-5055 (2001).

Kukita and Kukita, "Invited Review. Osteoclast differentiation antigen", *Histology and Histopathology*, 11:821-830 (1996).

Lacey et al., "Osteoprotegerin Ligand Is a Cytokine that Regulates Osteoclast Differentiation and Activation", *Cell*, 93(2)165-176 (1998).

Libermann and Baltimore, "Activation of interleukin-6 gene expression through the NF-kappa B transcription factor", *Mol. Cell. Biol.*, 10 (5):2327-2334 (1990).

Marie et al., "In vitro production of cytokines by bone surface-derived osteoblastic cells in normal and osteoporotic postmenopausal women: relationship with cell proliferation", *J Clin Endocrinol Metab*, 77(3):824-830 (1993).

Mc Hugh et al., "Receptor activator of NF-κB ligand arrests bone growth and promotes cortical bone resorption in growing rats", *J Appl Physiol* 95: 672-676 (2003).

Mee et al., "Dogs, Distemper and Paget's Disease", *BioEssays*, 15(12):783-789 (1993).

O'Dowd et al., "Site-directed mutagenesis of the cytoplasmic domains of the human beta 2-adrenergic receptor. Localization of regions involved in G protein- receptor coupling", *J. Biol. Chem.*, 263(31):15985-15992 (1988).

Pacifici et al., "Spontaneous Release of Interleukin 1 from Human Blood Monocytes Reflects Bone Formation in Idiopathic Osteoporosis", *PNAS*, 84(13): 4616-4620 (1987).

Pacifici et al., "Effect of Surgical Menopause and Estrogen Replacement on Cytokine Release from Human Blood Mononuclear Cells", *PNAS*, 88(12): 5134-5138 (1991).

Schoppet et al., "RANK Ligand and Osteoprotegerin: Paracrine Regulators of Bone Metabolism and Vascular Function", *Arterioscler Thromb Vasc Biol.*, 22:549-553 (2002); published online before print Jan. 31, 2002, doi:10.1161/01.ATV.0000012303.37971. DA.

Simonet et al., "Osteoprotegerin: A Novel Secreted Protein Involved in the Regulation of Bone Density" *Cell*, 89(2):309-319 (1997).

Suda et al., "Modulations of Osteoclast Differentiation", *Endocrine Reviews*, 13(1):66-80 (1992).

Suda et al., "Modulations of Osteoclast Differentiation: Update 1995", *Endocrine Reviews*, 4(1):266-270 (1995).

Suda et al., "Modulations of Osteoclast Differentiation by Local Factors", *Bone*, 17(2, Supp.):87S-91S (1995).

Takahashi et al., "A New Member of Tumor Necrosis Factor Ligand Family, ODF/OPGL/TRANCE/RANKL, Regulates Osteoclast Differentiation and Function", *Biochemical and Biophysical Research Communications*, 256(3):449-455 (1999).

Tashjian et al., "Tumor Necrosis Factor-α (Cachectin) Stimulates Bone Resorption in Mouse Calvaria via a Prostaglandin-Mediated Mechanism", *Endocrinology*, 120(5):2029-2036 (1987).

Thomson et al., "Osteoblasts mediate interleukin 1 stimulation of bone resorption by rat osteoclasts", *J. Exp. Med.*, 164(1):104-112 (1986).

Thomson et al., "Tumor necrosis factors alpha and beta induce osteoblastic cells to stimulate osteoclastic bone resorption", *J. Immunol.*, 138(3):775-779 (1987).

Tsuda et al., "Isolation of a Novel Cytokine from Human Fibroblasts That Specifically Inhibits Osteoclastogenesis", *Biochemical and Biophysical Research Communications*, 234(1):137-142 (1997).

Wong et al., "TRANCE Is a Novel Ligand of the Tumor Necrosis Factor Receptor Family That Activates c-Jun N-terminal Kinase in T Cells", *J. Biol. Chem.*, 272(40):25190-25194 (1997).

Yasuda et al., "Identity of Osteoclastogenesis Inhibitory Factor (OCIF) and Osteoprotegerin (OPG): A Mechanism by which OPG/OCIF Inhibits Osteoclastogenesis in Vitro", *Endocrinology*, 139(3):1329-1337 (1998).

Yasuda et al., "Osteoclast differentiation factor is a ligand for osteoprotegerin/osteoclastogenesis-inhibitory factor and is identical to TRANCE/RANKL", *Proc. Natl. Acad. Sci. USA*; 95(7):3597-3602 (1998).

* cited by examiner

US 7,462,700 B2

CANINE RANKL AND METHODS FOR PREPARING AND USING THE SAME

CROSS-REFERENCE TO RELATED APPLICATIONS

This application is a national stage filing of International Application No. US2003/039292, filed on Dec. 10, 2003 that claims priority under 35 U.S.C. § 119(e) of provisional application U.S. Ser. No. 60/432,092 filed Dec. 10, 2002, the contents of which are hereby incorporated by reference in its entirety.

FIELD OF THE INVENTION

The present application relates to nucleic acids encoding canine RANK ligand (RANKL) polypeptides, canine RANKL polypeptides, immunogenic compositions and/or vaccines comprising canine RANKL polypeptides, antagonists of canine RANKL, methods for identifying antagonists of canine RANKL, and methods for treating RANKL-mediated medical conditions.

BACKGROUND OF THE INVENTION

Bone tissue is a composite of proteins, cells and minerals known as bone matrix. In a living animal, cells called osteoblasts build bone matrix and cells called osteoclasts break down and resorb bone matrix. Osteoblasts arise from mesenchymal stem cells and produce bone matrix during development, after bone injury, and during the normal bone remodeling that occurs throughout life. Osteoclasts differentiate from hematopoietic precursors of the monocyte-macrophage lineage and resorb bone matrix to support normal bone remodeling, in response to injury or stress, and in response to various disease states.

The equilibrium between the construction and resorption of bone matrix is regulated by numerous factors. One of the systems that regulates bone physiology is the OPG/RANKL/RANK system. This system includes three factors: osteoprotegerin ("OPG"); receptor activator of NF-κB ("RANK"); and RANK ligand "RANKL").

RANK ligand, or RANKL, also variously art-known as ODF (osteoclast differentiation factor), OPGL (osteoprotegerin ligand) and TRANCE (TNF-related activation-induced cytokine), and by other designations, is a member of the TNF ligand family. RANKL exists in two forms: a cellular membrane-bound form and a soluble form. RANKL mRNA exhibits its highest level of expression in bone. The major role of RANKL in bone is to stimulate osteoclast differentiation and activity, and to inhibit osteoclast apoptosis. In the presence of low levels of macrophage-colony stimulating factor (M-CSF), RANKL appears to be both necessary and sufficient for the complete differentiation of osteoclast precursor cells into mature osteoclasts. RANKL mRNA is also expressed in lymphoid tissues, such as the lymph node, thymus, spleen, fetal liver and Peyer's patches. In addition, RANKL has a number of effects on immune cells. These effects include the activation of c-Jun N-terminal kinase (JNK) in T cells, inhibition of apoptosis of dendritic cells, induction of cluster formation by dendritic cells and effects on cytokine-activated T cell proliferation.

The RANKL/RANK signaling pathway has been characterized. RANKL, expressed on the surface of pre-osteoblast/stromal cells or in soluble form, binds to RANK, which is expressed on osteoclast precursor cells. This binding promotes the differentiation of osteoclast precursor cells into mature osteoclasts. Macrophage colony stimulating factor (M-CSF), which binds to its receptor, c-Fms, on preosteoclastic cells, appears to be involved in osteoclast development because it is the primary determinant of the pools of these precursor cells. OPG is a soluble receptor for RANKL, and can block the effects of RANKL by acting as a "decoy" binding target. In addition, a number of cytokines, including TNF-α and IL-1, modulate the system, for example, by stimulating M-CSF production or by increasing RANKL expression.

Proper functioning of the OPG/RANKL/RANK system is essential for bone metabolism, immune functions and vascular functions. Disruptions in this system have been implicated in various skeletal and immune disorders, such as rheumatoid arthritis, osteoporosis and osteopetrosis. Antagonists of RANKL can be used to treat osteoporosis and other conditions mediated by such RANKL/RANK interactions. Assays for the identification of such antagonists to human, mouse and rat RANKL have been enabled by the isolation of human, mouse and rat RANKL polypeptides. Because the antigenic (extracellular) domain of RANKL varies among species, species specific RANKL polypeptides are preferred for identifying species specific RANKL antagonists.

The RANKL proteins and encoding genes for several mammalian species are known. For example, human RANKL protein and encoding nucleic acid is described, for example, by U.S. Pat. No. 6,242,213. Rat RANKL protein and encoding nucleic acid is described, for example, by International published patent appl. No. WO 01/23549. Murine RANKL protein and encoding nucleic acid is described, for example, by co-owned U.S. Pat. No. 6,242,586. Methods of modulating the effects of RANKL from several non-canine sources are described, for example, by co-owned U.S. Pat. No. 6,525,180, by 6,316,408, and by Halkier et al., in published international patent application (WO0015807A1, March 2000), However, there remains a longfelt and heretofore unmet need in the art for the identification and production of canine RANKL, as well as for new methods and antagonists for modulating the effects of canine RANKL in canine and other animal, e.g., mammalian species.

The citation of any reference herein should not be construed as an admission that such reference is available as "prior art" to the instant application.

SUMMARY OF THE INVENTION

These and other problems are solved by the instant invention, that provides for nucleic acids encoding substantially all of the canine RANKL polypeptide, and methods of making and using the same. In particular, the present invention provides for an isolated nucleic acid molecule, and its complement, that includes a nucleic acid sequence encoding a polypeptide, wherein the encoded polypeptide includes amino acid residues according to SEQ ID NO:2. The present invention also provides a nucleic acid molecule that hybridizes to the complement of the isolated nucleic acid molecule under stringent conditions, provided that the hybridizable nucleic acid molecule does not encode a human, murine or rat RANKL. The artisan will appreciate that the isolated nucleic acid molecule of the present invention is optionally DNA or RNA.

The present invention also provides an isolated canine RANKL polypeptide according to SEQ ID NO:2, or a fragment thereof, that binds to canine RANK. Fragments of the canine RANKL polypeptide include any antigenic fragments, and preferably those enumerated by Tables 1 and 2, shown herein, below.

The present invention further provides immunogenic compositions that include the canine RANKL polypeptide, and the previously mentioned fragments thereof.

The present invention still further provides an immunogenic composition that includes the canine RANKL polypeptide, and/or an antigenic fragment thereof, e.g., listed by Tables 1 and 2, herein, below. The immunogenic composition is preferably in a vaccine composition, optionally including a suitable pharmaceutically acceptable carrier, i.e., comprising isotonic saline, physiologically acceptable buffer(s) and an effective art-known adjuvant, as required. More preferably, the immunogenic composition also includes at least one additional element incorporated into an immunogenic composition and/or into a fusion protein or a covalent conjugate linking the additional element to the canine RANKL polypeptide or fragment. The additional element can be at least one of the following and/or any combination thereof:

(a) at least one foreign T helper lymphocyte epitope,
(b) at least one element that targets the canine RANKL immunogenic composition to an antigen presenting cell or a B-lymphocyte,
(c) at least one element that stimulates the immune system,
(d) at least one element that optimizes presentation of the canine RANKL to the immune system.

The present invention also provides a polyclonal or monoclonal antibody or a functional fragment thereof that selectively binds to canine RANKL, and optionally RANKL of other animals, e.g., other mammals. Methods for inhibiting RANKL activity in an animal, e.g., a mammal, by administering to the animal an amount of the antibody or fragment thereof that is effective to inhibit RANKL activity in the mammal, are also provided.

The artisan will appreciate that the antibody is administered at a frequency and for a duration sufficient to maintain bone mass and/or bone density in the mammal at a level equal to or greater than the bone mass or bone density measured prior to the step of administering the antibody and/or fragment thereof.

In addition to employing the anti-RANKL antibodies of the present invention to treat or inhibit the loss of bone minerals in an animal such as a mammal, and particularly a canine, such antibodies can be elicited in situ by immunizing the animal to be treated with canine RANKL, or fragments thereof, with an immunogenic form of the canine RANKL. The present invention further provides methods for inhibiting RANKL activity in a mammal that comprise administering to the mammal an amount of a RANKL immunogenic composition capable of effectively eliciting antibodies that selectively bind to RANKL in the mammal. Such a RANKL immunogenic composition can either comprise or consist of a polypeptide having the amino acid sequence of SEQ ID NO:2, or a fragment thereof. The fragment of the polypeptide having the amino acid sequence of SEQ ID NO:2 in this case would be both capable of binding the canine receptor activator of NF-κB, and of effectively eliciting antibodies that selectively bind to RANKL in the mammal. Mammals that can be treated by direct administration of an antibody of the present invention or its functional equivalent, and/or through immunization as provided above, include, but are not limited to, a canine, an equine, a feline, a bovine, a porcine, and a human.

Also provided are nucleic acids, either RNA or DNA, encoding canine RANKL and fragments thereof, e.g., the polypeptide fragments listed by Tables 1 and 2, herein, below, replicable nucleic acid vectors, host cells comprising the vectors, and methods of producing the inventive polypeptide(s) by culturing the host cells under conditions suitable for expression the polypeptide. The vector can be a plasmid, a phage, a cosmid, a mini-chromosome, and a virus, suitable for prokaryotic or eukaryotic host cell (e.g., a bacterium, a yeast, a protozoan, a fungus, an insect cell, a plant cell, and a mammalian cell).

In particular, the replicable vector includes a suitable promotor operably linked 5' to the open reading frame of the canine RANKL immunogenic composition of interest. The present invention further provides stable cell lines comprising a replicable vector of the present invention. Such cell lines can secrete and/or express on its surface, a canine RANKL polypeptide, a fragment thereof, a fusion protein comprising the RANKL polypeptide or fragment thereof, or any other expressible canine RANKL immunogenic composition.

These and other aspects of the present invention will be better appreciated by reference to the following Detailed Description.

DETAILED DESCRIPTION OF THE INVENTION

Accordingly, the present invention provides for nucleic acid molecules encoding substantially all of the canine RANKL polypeptide, including the entire extracellular (antigenic) portion of the protein. The canine RANKL is a type II membrane protein having an N-terminal intracellular domain (approximately 48 amino acids) followed by a transmembrane domain (amino acids 49-68) and an extracellular domain (amino acids 69-319). The nucleic acid sequence and the corresponding amino acid sequence encoding the extracellular domain, transmembrane domain and a portion of the intracellular domain of the canine RANK ligand is defined by SEQ ID NO: 1 and SEQ ID NO: 2, respectively. Specifically, the nucleic acid and amino acid sequences for canine RANKL are complete, except for the first 129 nucleotides of the nucleic acid and corresponding 43 amino acids of the polypeptide.

The nucleic acid molecules of the present invention were isolated from an activated canine splenocyte cDNA library. The library may either be obtained commercially, or constructed according to methods known in the art. Simply by way of example, a suitable cDNA library is optionally constructed by producing 3W Th1 or Th2 cells as described, e.g., in Openshaw, et al. (1995) *J. Exp. Med.* 182:1357-1367, incorporated by reference herein in its entirety. Briefly, Th1 or Th2 populations are derived from canine CD4+ T cells stimulated with antigen and antigen presenting cells in the presence of IL-12 or IL-4. Cells are stimulated once each week for 3 weeks, then harvested and restimulated, e.g., with PMA and ionomycin for 4 h. See, Murphy, et al. (1996) *J. Exp. Med.* 183: 901-913. Preferably, the cDNA library is prepared by the method of Bolin et al., (1997), *The Journal of Neuroscience*, 17(14):5493-5502, incorporated by reference herein its entirety.

Total RNA is isolated from the harvested cells using standard methods known in the art, e.g., using the guanidine thiocyanate/CsCl gradient procedure as described by Chirgwin, et al. (1978) *Biochem.* 18:5294-5299. Poly(A) +RNA is isolated using, e.g., the OLIGOTEX mRNA isolation kit (QIAGEN). RNA from these cells is used to synthesize first strand cDNA, e.g., by using NotI/Oligo-dT primer (Gibco-BRL, Gaithersburg, Md.). Double-stranded cDNA is synthesized, ligated with BstXI adaptors, digested with NotI, size fractionated for >0.5 kilobase pairs (kb) and ligated into the NotI/BstXI sites of pJFE-14, a derivative of the pCDSRα vector. See, for instance, Takebe, et al. (1985) *Mol. Cell Biol.* 8:466-472. Electro-competent *E. coli* DH10α cells (Gibco-BRL) are used for transformation.

Canine RANKL was therefore cloned from a canine splenocyte cDNA library by employing a strategy of conducting a series of nested PCR reactions. Nested PCR involves two sequential PCR reactions, where the first reaction product provides guidance for designing the primers for the next PCR reaction. Each PCR reaction described in Example 1, below, generally contained 0.02 µg/µl of nucleic acid template, 1X PCR buffer, 0.8 mM dNTP's, 1.1 mM Mg(OAC)$_2$, 0.16 units/µl of rTth polymerase (recombinant thermostable Taq polymerase), 2 OD/ml of vector primer, and 0.2 OD/ml of gene specific primer. The nested PCR was performed, starting with the canine splenocyte activated cDNA library, using a GeneAmp XL PCR kit (Perkin Elmer, Branchburg, N.J.).

In the initial reaction, 30 cycles of PCR were performed using a vector specific primer and a gene specific primer (same or cross-species primer). The PCR reaction was conducted with cycling between 94° C. (for 1 minute) and 65° C. (for 5 minutes) for 30 cycles, followed by heating to 72° C. for 10 minutes. Subsequently, a small aliquot of the PCR product of the first reaction served as the template for a second PCR reaction.

The second PCR reaction used gene specific primers (same or cross species) that hybridized to sequences internal to or nested between the first set of primers. This is called double nesting. The second PCR reaction was cycled according to the same protocol as the first reaction. However, in some cases, the first reaction gene specific primer was used in the second set of reactions with a different gene specific primer (same or cross species) for a single nesting reaction.

To provide a better appreciation of the present invention, the following terms are defined.

As used herein, the terms "canine RANK ligand" and "canine RANKL" are defined to mean any molecule capable of specifically binding to the canine RANK receptor. Thus, the definition includes a canine RANKL polypeptide that includes the peptide sequence defined by SEQ ID NO: 2 or a portion thereof, while optionally avoiding 100% homology with other art-known RANKL polypeptides isolated from non-canine mammalian species, e.g., optionally excluding the specific nucleic acid and/or polypeptide sequences encoding human RANKL, murine RANKL, rat RANKL, and/or any other RANKL species that are presently art-known.

As used herein, the term "isolated" means that the referenced material is removed from the environment in which it is naturally found. Thus, an isolated biological material can be free of cellular components, i.e., components of the cells in which the material is found or produced. In the case of nucleic acid molecules, an isolated nucleic acid includes a PCR product, an isolated mRNA, cDNA or restriction fragment. In another embodiment, an isolated nucleic acid is preferably excised from the chromosome in which it may be found, and more preferably, is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns, e.g., a cDNA. Isolated nucleic acid molecules are also contemplated to include sequences inserted into plasmids, cosmids, artificial chromosomes and the like. Thus, in a specific embodiment, a recombinant nucleic acid is an isolated nucleic acid. In certain embodiments, it is useful to allow an isolated protein or nucleic acid to associate with other proteins or nucleic acids, or both, or with cellular membranes if it is a membrane-associated protein in order to achieve a desirable utility. An isolated material may be, but need not be, purified.

The terms "purified" or "isolated" as employed herein refers to materials separated under conditions that reduce or eliminate the presence of unrelated materials, i.e., contaminants, including native materials from which the material is obtained. For example, a purified or isolated protein is preferably free of other proteins or nucleic acids with which it can be found within a cell. A purified material may contain less than about 50%, preferably less than about 75%, and most preferably less than about 90%, of the cellular components with which it was originally associated. Purity can be evaluated by chromatography, gel electrophoresis, immunoassay, composition analysis, biological assay and other methods known in the art.

Methods for purification are well-known in the art. For example, nucleic acids can be purified by precipitation, chromatography, ultracentrifugation and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction and countercurrent distribution. For some purposes, it is preferable to produce the polypeptide in a recombinant system in which the protein contains an additional sequence tag that facilitates purification, such as, but not limited to, a polyhistidine sequence or a sequence that specifically binds to an antibody, such as FLAG and GST. The polypeptide can then be purified from a crude lysate of the host cell by chromatography on an appropriate solid-phase matrix. Alternatively, antibodies produced against the protein or against a peptide derived therefrom can be used as purification reagents.

The term "substantially pure" indicates the highest degree of purity which can be achieved using conventional purification techniques known in the art and means a canine RANKL polypeptide, nucleic acid or other material that is free from other contaminating proteins, nucleic acids and other biologicals derived from an original source organism or recombinant DNA expression system. Substantial purity may be assayed by standard methods and will typically exceed at least about 75%, preferably at least about 90%, more preferably at least about 95% and most preferably at least about 99% purity. Purity evaluation may be made on a mass or molar basis.

A "polypeptide" is a chain of amino acids that are linked together by peptide bonds. Optionally, a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

Further the use of singular terms for convenience in description is in no way intended to be so limiting. Thus, for example, reference to a composition comprising "an antibody" includes reference to one or more of such antibodies. It is also to be understood that the present invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

Preferably, a polypeptide according to the present invention is the canine RANK ligand having an amino acid sequence defined by SEQ ID NO: 2. Alternatively, a polypeptide comprises a subsequence of the amino acid sequence defined by SEQ ID NO: 2 containing at least about 8, preferably at least about 12, more preferably at least about 20, and most preferably at least about 30 or more contiguous amino acid residues, up to and including the total number of residues in the ligand. The polypeptides of the present invention can comprise any part of the sequence of such a ligand, and especially those fragments that have heretofore not been known to the art. Polypeptides can be produced by proteolytic cleavage of an intact ligand, by chemical synthesis or by the application of recombinant DNA technology. A polypeptide may be native or wild-type, meaning that it is identical to a polypeptide that occurs in nature; or it may be a mutein, a variant, an analog or otherwise modified, meaning that is has been made, altered, derived or is in some way different or changed from a native polypeptide.

The modifications that occur in a polypeptide are often a function of how the polypeptide is made. For canine RANK ligand polypeptides made by expressing a cloned gene in a host, for instance, the nature and extent of the modifications will be determined in large part by the host cell's post-translational modification capacity and the modification signals present in the amino acid sequence of the polypeptide. For example, glycosylation often does not occur in bacterial hosts, such as $E.\ coli$. Accordingly, when glycosylation is desired, a polypeptide should be expressed in a glycosylating host, generally a eukaryotic cell. Insect cells often carry out the same post-translational glycosylations as mammalian cells; for this reason, insect cell expression systems have been developed to efficiently express mammalian proteins having their native patterns of glycosylation. Similar considerations apply to other modifications. It will be appreciated that the same types of modifications may be present in the same or varying degrees at several sites within a given polypeptide. Also, a given polypeptide may contain many types of modifications.

Varients of the subject canine RANKL polypeptide and encoding nucleic acid(s) have several utilities. In one embodiment, the canine RANKL is modified to provide nonfunctional binding to the RANK binding-partner, resulting in a blocking of physiological response to canine RANKL polypeptides. The inventive canine RANKL polypeptide and fragments thereof therefore provide agents for screening assays to identify RANK competitive or noncompetitive antagonists of canine or non-canine RANK function. Thus, in vitro assays of the present invention will often use isolated protein, membranes from cells expressing a membrane associated recombinant canine RANKL polypeptide, soluble fragments comprising antigen binding segments of these proteins, or fragments attached to solid phase substrates. These assays will also allow for the diagnostic determination of the effects of either binding segment mutations and modifications, or antigen mutations and modifications, e.g., canine RANKL polypeptide analogs.

In an alternative embodiment, the inventive canine RANKL polypeptide and fragments thereof provide immunogens, i.e., the polypeptide and/or fragments thereof suitable for inducing a useful immune response in a mammal so treated. The resulting immunity will serve to provide a source for anti-canine RANK binding antibodies, anti-canine RANKL T-cells for generating useful mAb-producing hybridomas, and/or to downregulate RANK function in the treated mammal, thereby maintaining or enhancing bone density and/or bone strength in the treated mammal.

It should be noted that mammals exhibit tolerance to self proteins, thus administration, i.e., vaccination of a mammal of the canine species with canine RANKL polypeptide, by itself, without more, is not expected to provide a useful level of immunization. Several additional strategies are employed in order to present the inventive RANKL polypeptide to a mammalian immune system in a way that results in an effective immune response.

In one preferred embodiment, the inventive canine RANKL polypeptide is administered with suitable adjuvants, in order to present the polypeptide epitopes to the immune system in a way that is recognized as "foreign" or non-self. In another preferred embodiment, the inventive canine RANKL polypeptide or fragments thereof are modified by any art-known mutagenesis method to render it more antigenic to a canine species mammal. In a further preferred embodiment, all or part of the inventive RANKL polypeptide is joined by chemical synthetic or genetic engineering methods with one or more additional peptide domains to form an immunogenic fusion protein for administration to canines or other mammalian or avian species.

In yet a further embodiment, canine RANKL polypeptide is employed to elicit an immune response in a non-canine animal, including mammals, and particularly humans. For example, human, mouse, rat and canine RANKL polypeptide are not fully homologous. Thus, the canine RANKL polypeptide provides a natural immunogen that is recognized as foreign, or non-self, by the equine, feline, bovine, porcine, and human immune systems for example, without further modification or variation being required. Of course, administration of canine RANKL polypeptide or fragments thereof to a non-canine mammal or to an avian (for enhancing egg production), will optionally be in combination with a suitable vaccine composition, including adjvants, and the like, as discussed in more detail herein, below.

For those embodiments of the present invention that comprise canine RANKL variants, the term "Variant(s)", is used herein to describe polynucleotides or polypeptides that differ from a reference polynucleotide or polypeptide respectively. The term variants include physical variants, such as sequence variants and post-translational variants, and functional variants, such as analogs. Variants in this sense are described below and elsewhere in the present disclosure in greater detail.

Glycosylation variants include, e.g., variants made by modifying glycosylation patterns during synthesis and processing in various alternative eukaryotic host expression systems, or during further processing steps. Particularly preferred methods for producing glycosylation modifications include exposing the canine RANK ligand to glycosylating enzymes derived from cells that normally carry out such processing, such as mammalian glycosylation enzymes. Alternatively, deglycosylation enzymes can be used to remove carbohydrates attached during production in eukaryotic expression systems.

(1) A variant can be a polynucleotide that differs in nucleotide sequence from a reference polynucleotide. Changes in the nucleotide sequence of the variant may be silent, i.e., they do not alter the amino acid sequence encoded by the polynucleotide. Where alterations are limited to silent changes of this type, a variant will encode a polypeptide with the same amino acid sequence as the polypeptide encoded by the reference polynucleotide. However, changes in the nucleotide sequence of the variant may alter its amino acid sequence. Such nucleotide changes may result in amino acid substitutions, additions, deletions, fusions and truncations in the polypeptide encoded by the reference sequence, as discussed below.

(2) Alternatively, a variant may be a polypeptide that differs in amino acid sequence from a reference polypeptide. Generally, differences are limited so that the amino acid sequences of the reference and the variant are closely similar overall and, in many regions, identical. Variant and reference polypeptides may differ in amino acid sequence by one or more substitutions, additions, deletions, fusions and truncations, which may be present in any combination.

(3) A variant may also be a fragment of a polynucleotide or polypeptide that differs from a reference polynucleotide or polypeptide sequence by being shorter than the reference sequence, such as by a terminal or internal deletion. A variant of a polypeptide also includes a polypeptide which retains essentially the same biological function or activity as such polypeptide, e.g., pro-proteins which can be activated by cleavage of the pro-protein portion to produce an active mature polypeptide.

(4) A variant may also be (i) one in which one or more of the amino acid residues are substituted with a conserved or non-conserved amino acid residue (preferably a conserved amino acid residue) and such substituted amino acid residue may or may not be encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which additional amino acids are fused to the mature polypeptide, such as a leader or secretory sequence or a sequence which is employed for purification of the mature polypeptide or a pro-protein sequence.

(5) Furthermore, a variant of the polynucleotide or polypeptide may be a naturally occurring variant, such as a naturally occurring allelic variant, or it may be a variant that is not known to occur naturally. Such non-naturally occurring variants of the polynucleotide may be made by mutagenesis techniques, including those applied to polynucleotides, cells or organisms, or may be made by recombinant means. Among polynucleotide variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

All such variants defined above in (1)-(5) are deemed to be within the scope of those skilled in the art, except that RANKL polypeptide variants that are 100% homologous to human RANKL, murine RANKL, rat RANKL and/or any other heretofore art-known non-canine RANKL polypeptides, and/or art-known non-canine RANKL-encoding nucleic acids, are preferably excluded from the scope of the present invention.

The present application also encompasses analogs of the canine RANK ligand. The term "analog(s)" means a RANK ligand of the present invention which has been modified by deletion, addition, modification or substitution of one or more amino acid residues in the wild-type canine ligand. It encompasses allelic and polymorphic variants, and also muteins and fusion proteins which comprise all or a significant part of such canine RANK ligand, e.g., covalently linked via a side-chain group or terminal residue to a different protein, polypeptide or moiety (fusion partner).

Some analogs are truncated variants in which residues have been successively deleted from the amino- and/or carboxy-termini, while substantially retaining the characteristic RANK binding activity. Substantial retention of binding activity by the foregoing analogs of canine RANKL typically entail retention of at least about 50%, preferably at least about 75%, more preferably at least about 80%, and most preferably at least about 90% of the RANK binding activity and/or specificity of the corresponding wild-type ligand.

Modifications of amino acid residues may include, but are not limited to, aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine. Other analogs are canine RANK ligands containing modifications, such as the incorporation of unnatural amino acid residues or phosphorylated amino acid residues, such as phosphotyrosine, phosphoserine or phosphothreonine residues. Other potential modifications include sulfonation, biotinylation, or the addition of other moieties.

Some amino acid substitutions are preferably conservative, with residues replaced with physically or chemically similar residues, such as Gly/Ala, Asp/Glu, Val/Ile/Leu, Lys/Arg, Asn/Gln and Phe/Trp/Tyr. Analogs having such conservative substitutions typically retain substantial RANK binding activity. Other analogs, which have non-conservative substitutions, such as Asn/Glu, Val/Tyr and His/Glu, may substantially lack such activity. Nevertheless, such non-conservative analogs are useful because they can be used as antigens to elicit the production of antibodies in an immunologically competent host. Because these analogs retain many of the epitopes (antigenic determinants) of the wild-type ligands from which they are derived, many antibodies produced against them can also bind to the active-conformation or denatured wild-type ligands. Accordingly, such antibodies can also be used, e.g., for the immunopurification or immunoassay of the wild-type ligands.

Analogs of canine RANKL can be prepared by chemical synthesis or by using site-directed mutagenesis [Gillman et al., *Gene* 8:81 (1979); Roberts et al., *Nature,* 328:731 (1987) or Innis (Ed.), 1990, *PCR Protocols: A Guide to Methods and Applications*, Academic Press, New York, N.Y.] or the polymerase chain reaction method [PCR; Saiki et al., *Science* 239:487 (1988)], as exemplified by Daugherty et al. [*Nucleic Acids Res.* 19:2471 (1991)] to modify nucleic acids encoding the ligand. Adding epitope tags for purification or detection of recombinant products is also envisioned. General techniques for nucleic acid manipulation and expression that can be used to make the analogs are described generally, e.g., in Sambrook, et al., *Molecular Cloning: A Laboratory Manual* (2d ed.), 1989, Vols. 1-3, Cold Spring Harbor Laboratory. Techniques for the synthesis of polypeptides are described, for example, in Merrifield, *J. Amer. Chem. Soc.* 85:2149 (1963); Merrifield, *Science* 232:341 (1986); and Atherton et al., *Solid Phase Peptide Synthesis: A Practical Approach,* 1989, IRL Press, Oxford. Still other analogs are prepared by the use of agents known in the art for their usefulness in cross-linking proteins through reactive side groups. Preferred derivatization sites with cross-linking agents are free amino groups, carbohydrate moieties and cysteine residues. In an optional embodiment, RANKL polypeptide analogs that are 100% homologous to human RANKL, murine RANKL, rat RANKL and/or any other heretofore art-known non-canine RANKL polypeptides, and/or art-known non-canine RANKL encoding nucleic acids, are excluded from the scope of the present invention.

Preferred polypeptide fragments of SEQ ID NO:2 are antigenic, and will induce a protective immunity in a mammal, canine or other species, when administered in a form suitable for inducing an effective immune response that inhibits the in vivo activity of endogenous RANKL protein, to provide desirable benefits, such as maintaining or increasing bone mineral density or strength. Polypeptide fragments preferably include, for example, those listed by Table 1, below.

TABLE 1

From about residue 10 to about residue 275 of SEQ ID NO: 2;
From about residue 30 to about residue 275 of SEQ ID NO: 2;
From about residue 50 to about residue 275 of SEQ ID NO: 2;
From about residue 150 to about residue 275 of SEQ ID NO: 2;
From about residue 250 to about residue 275 of SEQ ID NO: 2;
From about residue 255 to about residue 275 of SEQ ID NO: 2;
From about residue 235 to about residue 255 of SEQ ID NO: 2;
From about residue 215 to about residue 235 of SEQ ID NO: 2;
From about residue 195 to about residue 215 of SEQ ID NO: 2;
From about residue 175 to about residue 195 of SEQ ID NO: 2
From about residue 155 to about residue 175 of SEQ ID NO: 2;
From about residue 135 to about residue 155 of SEQ ID NO: 2;
From about residue 95 to about residue 135 of SEQ ID NO: 2;
From about residue 75 to about residue 95 of SEQ ID NO: 2;
From about residue 55 to about residue 75 of SEQ ID NO: 2;
From about residue 35 to about residue 55 of SEQ ID NO: 2;
From about residue 15 to about residue 35 of SEQ ID NO: 2;
From about residue 1 to about residue 15 of SEQ ID NO: 2;
as well as combinations of the foregoing.

The present invention is also contemplated to include recombinant proteins, e.g., heterologous fusion proteins comprising, e.g., fragments of polypeptide of SEQ ID NO:2, e.g., including the above-enumerated polypeptide fragments. A heterologous fusion protein is a fusion of proteins or segments which are naturally not normally fused in the same manner. A similar concept applies to heterologous nucleic acid sequences, e.g., nucleic acid molecule(s) encoding SEQ ID NO:2, e.g., including nucleic acid molecules encoding the above-enumerated polypeptide fragments. Fusion proteins will be useful as sources for cleaving, separating, and purifying portions thereof.

Fusion proteins comprising canine RANKL polypeptides and other homologous or heterologous proteins are prepared by recombinant and/or synthetic peptide methods to include, e.g., a reporter polypeptide, e.g., luciferase, with a segment or domain of a protein, e.g., a receptor-binding segment, so that the presence or location of the fused ligand may be easily determined. See, e.g., Dull, et. al., U.S. Pat. No. 4,859,609. Other desirable fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski, et. al. (1988) Science 241:812-816.

In addition, fusion proteins comprise operatively linking similar functional domains from other proteins using art-known methods. For example, target-binding or other segments may be "swapped" between different new fusion polypeptides or fragments. See, e.g., Cunningham, et al. (1989) Science 243:1330-1336; and O'Dowd, et al. (1988) *J. Biol. Chem.* 263:15985-15992, as well as the fusion murine RANKL constructs described by co-owned U.S. Pat. Nos. 6,242,586, and 6,525,180, the disclosures of which are incorporated by reference herein. The above-provided fragments of SEQ ID NO:2 are preferably incorporated into a fusion protein to provide an immunogenic fusion protein useful in preparing an immunogenic composition and/or vaccine.

The phosphoramidite method described by Beaucage and Carruthers (1981) *Tetra. Letts.* 22:1859-1862, will also produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques. Other methods of producing fusion proteins are known, including those taught by published U.S. Patent Appl. No. 20030165996, and published WO0015807A1, the disclosures of which are incorporated by reference herein.

For example, a canine RANKL fusion protein immunogen based on the polypeptide or polypeptide fragment of SEQ ID NO:2, includes the following modifications and/or features added to SEQ ID NO: 2 or a fragment thereof
  (a) at least one foreign T helper lymphocyte epitope,
  (b) at least one element that targets the canine RANKL immunogen to an antigen presenting cell or a B-lymphocyte,
  (c) at least one element that stimulates the immune system,
  (d) at least one element that optimizes presentation of the canine RANKL polypeptide to the immune system, and/or combinations thereof.

Preferably, a substantial fraction of the original B-lymphocyte epitopes of the RANKL polypeptide are retained.

In one preferred embodiment, side groups, e.g., foreign T-cell epitopes or the first, second and third moieties noted above, are covalently or non-covalently attached to the canine RANKL polypeptide. This is accomplished by derivatizing one or more amino acid residues of the RANKL polypeptide without altering the primary amino acid sequence, and/or without introducing changes in the peptide bonds between the individual polypeptide residues.

An alternative preferred embodiment provides for canine RANKL immunogens wherein the polypeptide of SEQ ID NO:2 is more extensively modified by recombinant or peptide synthetic methods, e.g., by preparing deletion or insertion muteins or fusion polypeptides. For example, WO 95/05849, the disclosure of which is incorporated by reference herein in its entirety, describes a method for down-regulating self-proteins by immunising an animal with analogs of the self-proteins. The analogs are prepared by substituting parts of the polypeptide of interest with a corresponding number of amino acid sequence(s) that comprise a foreign immunodominant T-cell epitope, while at the same time maintaining the overall tertiary structure of the self-protein in the analog. The modification can be provided by insertion, addition, deletion or substitution of the amino acid residues of SEQ ID NO:2 in order to provide a RANKL immunogen comprising a foreign T-cell epitope while retaining sufficient B-cell epitopes of SEQ ID NO:2. Preferably, the overall tertiary structure of the canine RANKL polypeptide is maintained.

The present invention contemplates modified canine RANKL immunogens obtained by deletions of those domains of the canine RANKL sequence which e.g., exhibit adverse effects in vivo and/or deletion of domains that are normally located intracellularly, and thus could give rise to undesirable immunological reactions.

Canine RANKL immunogens retaining a substantial fraction of B-cell epitopes and the overall tertiary structure of native canine RANKL polypeptide or an immunogenic portion thereof, can be attained in a number of ways, even for a polypeptide modified by the methods described supra. One such method comprises preparing an anti-canine RANKL polyclonal anti-serum to provide a test reagent (e.g., in a competitive ELISA) against the modified canine RANKL polypeptides. Analogs that react to the same extent with the antiserum as does canine RANKL can be considered to have the same overall tertiary structure as does native canine RANKL. Further, modified canine RANKL polypeptides exhibiting a limited (but still significant and specific) reactivity with such an antiserum are regarded as having maintained a substantial fraction of the original B-cell epitopes.

An alternative preferred method provides for monoclonal antibodies reactive with distinct epitopes of canine RANKL that are prepared and used in a test panel. This approach has the advantage of allowing (1) epitope mapping of canine RANKL and (2) mapping of the epitopes which are maintained in the analogs prepared.

Yet another alternative method provides for resolving the 3-dimensional structure of canine RANKL polypeptide, or of a biologically active truncate thereof that is compared to the resolved three-dimensional structure of each of the modified polypeptides. Three-dimensional structural determinations can be made through X-ray diffraction studies, NMR-spectroscopy, and/or by circular dichroism studies.

Nucleic Acids and Expression Vectors

The terms "polynucleotide" or "nucleic acid", as used herein, refer to a series of nucleotides, e.g., deoxyribonucleic acid or ribonucleic acid bases, bound to a polymer backbone. These include, for example, genomic DNA, cDNA, RNA, mRNA, any synthetic and genetically manipulated polynucleotides, and both sense and antisense polynucleotides. This term also includes single and double stranded molecules; i.e., DNA-DNA, DNA-RNA and RNA-RNA hybrids. Typical nucleotides include inosine, adenosine, guanosine, cytosine, uracil and thymidine. However, nucleic acids may also contain modified nucleotide bases, for example, thio-uracil, thio-guanine and fluor-uracil.

A polynucleotide or nucleic acid may be flanked by natural regulatory sequences or may be associated with heterologous sequences, including promoters, enhancers, response elements, signal sequences, polyadenlation sequences, introns, 5' and 3' non-coding regions and the like. The nucleic acids may also be modified by any means known in the art. Non-limiting examples of such modification include methylation, caps and substitution of one or more of the naturally occurring nucleotides with an analog. Polynucleotides may contain one or more additional covalently linked moieties, such as proteins, intercalators, chelators and alkylators. Furthermore the polynucleotides may also be modified with a label capable of providing a detectable signal, either directly or indirectly. Exemplary labels include radioisotopes, fluorescent molecules, biotin and the like.

The term "recombinant" defines a biological material (e.g., a nucleic acid or polypeptide) either by its method of production or its structure. For example, some recombinant nucleic acids are made by the use of recombinant DNA techniques which involve human intervention, either in manipulation or selection. Other recombinant nucleic acids are made by fusing two nucleotide fragments that are not naturally contiguous to each other. Engineered vectors are encompassed, as well as nucleic acids comprising sequences derived using any synthetic oligonucleotide process.

The present invention further encompasses recombinant DNA molecules and fragments having sequences that are identical or highly homologous to those described herein, excluding those nucleotide sequences that encode human, murine, and rat RANKL.

"Identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Similarity" between two polypeptides is determined by comparing the amino acid sequence and its conserved amino acid substitutes of one polypeptide to the sequence of a second polypeptide. "Identity" and "similarity" can be readily calculated by known methods, including, but not limited to, those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48:1073 (1988). Preferred methods to determine identity are designed to give the largest match between the sequences tested.

By way of example, a polynucleotide sequence of the present invention may be identical to the reference sequence of SEQ ID NO: 1, that is it may be 100% identical, or it may include up to a certain integer number of nucleotide alterations as compared to the reference sequence such that the percent identity is less than 100% identity. Such alterations are selected form the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleotides in SEQ ID NO: 1 by the integer defining the percent identity divided by 100 and then subtracting that product from said total number of nucleotides in SEQ ID NO: 1, or $n_n = x_n - (x_n * y)$, wherein $n_n$ is the number of nucleotide alterations, $x_n$ is the total number of nucleotides in SEQ ID NO: 1, y is, for instance 0.70 for 70%, 0.80 for 80%, 0.85 for 85% etc., * is the symbol for the multiplication operator, and wherein any non-integer product of $x_n$ and y is rounded down to the nearest integer prior to subtracting it from $x_n$.

Preferred polypeptide embodiments further include an isolated polypeptide comprising a polypeptide having at least about 50, 60, 70, 80, 85, 90, 95, 97 or 100% identity to the polypeptide reference sequence of SEQ ID NO: 2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO: 2 by the integer defining the percent identity divided by 100 and then subtracting that product from said total number of amino acids in SEQ ID NO: 2, or $n_a = x_a - (x_a * y)$, wherein $n_a$ is the number of amino acid alterations, $x_a$ is the total number of amino acids in SEQ ID NO: 2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and * is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO: 2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given percent identity is determined by multiplying the total number of amino acids in SEQ ID NO: 2 by the integer defining the percent identity divided by 100 and then subtracting that product from said total number of amino acids in SEQ ID NO: 2, or $n_a = x_a - (x_a * y)$, wherein $n_a$ is the number of amino acid alterations, $x_a$ is the total number of amino acids in SEQ ID NO: 2, y is, for instance 0.70 for 70%, 0.80 for 80%, 0.85 for 85% etc., and * is the symbol for the multiplication operator, and wherein any non-integer product of $x_a$ and y is rounded down to the nearest integer prior to subtracting it from $x_a$.

The term "homology", as it is used herein, embraces both identity and similarity.

For example, some of the variants have substantial amino acid sequence homology with the amino acid sequence of the canine RANK ligand. In this invention, amino acid sequence homology or sequence identity is determined by optimizing residue matches and, if necessary, by introducing gaps as required. Homologous amino acid sequences are typically intended to include natural allelic, polymorphic and interspecies variations in each respective sequence. Typical homologous proteins or polypeptides will have from 25-100% homology (if gaps can be introduced) to 50-100% homology (if conservative substitutions are included) with the amino acid sequence of canine RANKL. Observed homologies will typically be at least about 35%, preferably at least about 50%, more preferably at least about 75%, and most preferably at least about 80% or more. See, Needleham et al., *J. Mol. Biol.* 48:443-453 (1970); Sankoff et al. in *Time Warps, String Edits, and Macromolecules: The Theory and Practice of Sequence Comparison,* 1983, Addison-Wesley, Reading, Mass.; and software packages from IntelliGenetics, Mountain View, Calif., and the University of Wisconsin Genetics Computer Group, Madison, Wis.

Homologous nucleic acid sequences are those which when aligned and compared exhibit significant similarities. Standards for homology in nucleic acids are either measures for homology generally used in the art by sequence comparison or based upon hybridization conditions, which are described in greater detail below.

Substantial nucleotide sequence homology is observed when there is identity in nucleotide residues in two sequences (or in their complementary strands) when optimally aligned to account for nucleotide insertions or deletions, in at least about 50%, preferably in at least about 75%, more preferably in at least about 90%, and most preferably in at least about 95% of the aligned nucleotides. Substantial homology also exists when one sequence will hybridize under selective hybridization conditions to another. Typically, selective hybridization will occur when there is at least about 55% homology over a stretch of at least about 30 nucleotides, preferably at least about 65% homology over a stretch of at least about 25 nucleotides, more preferably at least about 75% homology, and most preferably at least about 90% homology over about 20 nucleotides. See, e.g., Kanehisa, *Nucleic Acids Res.* 12:203 (1984). The lengths of such homology comparisons may encompass longer stretches and in certain embodiments may cover a sequence of at least about 17, preferably at least about 25, more preferably at least about 50, and most preferably at least about 75 nucleotide residues.

Stringency conditions employed in hybridizations to establish homology are dependent upon factors such as salt concentration, temperature, the presence of organic solvents and other parameters. Stringent temperature conditions usually include temperatures in excess of about 30° C., often in excess of about 37° C., typically in excess of about 45° C., preferably in excess of about 55° C., more preferably in excess of about 65° C. and most preferably in excess of about 70° C. Stringent salt conditions will ordinarily be less than about 1000 mM, usually less than about 500 mM, more usually less than about 400 mM, preferably less than about 300 mM, more preferably less than about 200 mM and most preferably less than about 150 mM. For example, salt concentrations of 100, 50 and 20 mM are used. The combination of the foregoing parameters, however, is more important than the measure of any single parameter. See, e.g., Wetmur et al., *J. Mol. Biol.* 31:349 (1968).

A further indication that two nucleic acid sequences encoding polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions.

Nucleic acids encoding canine RANKL or fragments thereof can be prepared by standard methods. For example, DNA can be chemically synthesized using, e.g., the phosphoramidite solid support method of Matteucci et al. [*J. Am. Chem. Soc.* 103:3185 (1981)], the method of Yoo et al [*J. Biol. Chem.* 764:17078 (1989)], or other well known methods.

Of course, due to the degeneracy of the genetic code, many different nucleotide sequences can encode the canine RANK ligand. The codons can be selected for optimal expression in prokaryotic or eukaryotic systems. Such degenerate variants are, of course, also encompassed by the present invention.

Moreover, nucleic acids encoding the canine RANK ligand can readily be modified by nucleotide substitutions, nucleotide deletions, nucleotide insertions, and inversions of nucleotide stretches. Such modifications result in novel DNA sequences that encode antigens having immunogenic or antigenic activity in common with the wild-type ligand. These modified sequences can be used to produce wild type or mutant ligands, or to enhance expression in a recombinant DNA system.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors that can be used in this invention include microbial plasmids, viruses, bacteriophage, integratable DNA fragments and other vehicles that may facilitate integration of the nucleic acids into the genome of the host. Plasmids are the most commonly used form of vector, but all other forms of vectors which serve an equivalent function and which are or become known in the art are suitable for use herein. See, e.g., Pouwels et al., *Cloning Vectors: A Laboratory Manual,* 1985 and Supplements, Elsevier, N.Y., and Rodriguez et al. (eds.), *Vec-* tors: *A Survey of Molecular Cloning Vectors and Their Uses,* 1988, Buttersworth, Boston, Mass.

Insertion of DNA encoding the canine RANK ligand into a vector is easily accomplished when the termini of both the DNA and the vector comprise compatible restriction sites. If this cannot be done, it may be necessary to modify the termini of the DNA and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). See, e.g., Saiki et al., *Science* 239:487 (1988). The cleaved vector and the DNA fragments may also be modified, if required, by homopolymeric tailing.

Recombinant expression vectors used in this invention are typically self-replicating DNA or RNA constructs comprising nucleic acids encoding one of the canine RANK ligands, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors may also contain an origin of replication that allows the vector to replicate independently of the host cell.

Expression of nucleic acids encoding the canine RANK ligand of this invention can be carried out by conventional methods in either prokaryotic or eukaryotic cells. The term "host cell" means any cell that can express a foreign gene, DNA or RNA sequence to produce a desired substance, such as an RNA or protein. Suitable host cells for expressing nucleic acids encoding canine RANKL include prokaryotes and higher eukaryotes. Prokaryotes include both gram negative and positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic expression control sequences typically used include promoters, including those derived from the β-lactamase and lactose promoter systems [Chang et al., *Nature,* 198:1056 (1977)], the tryptophan (trp) promoter system [Goeddel et al., *Nucleic Acids Res.* 8:4057 (1980)], the lambda $P_L$ promoter system [Shimatake et al., *Nature,* 292: 128 (1981)] and the tac promoter [De Boer et al., *Proc. Natl. Acad. Sci.* USA 292:128 (1983)]. Numerous expression vectors containing such control sequences are known in the art and commercially available.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express canine RANKL include, but are not limited to, those containing the lac promoter (pUC-series); trp promoter (pBR322-trp); lpp promoter (the pIN-series); lambda-pP or pR promoters (pOTS); or hybrid promoters such as ptac (pDR540). See, Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses,* 1988, Buttersworth, Boston, pp. 205-236.

Higher eukaryotic tissue culture cells are preferred hosts for the recombinant production of canine RANKL. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, Chinese hamster ovary (CHO) cell lines, baby rat kidney (BRK) cell lines, insect cell lines, bird cell lines, and monkey (COS) cell lines.

Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR®3.1, pcDNA1, pCD [Okayama et al., *Mol. Cell Biol.* 5:1136 (1985)], pMC1neo Poly-A [Thomas et al., *Cell* 51:503 (1987)], pUC19, pREP8, pSVSPORT and derivatives thereof, and baculovirus vectors, such as pAC 373 or pAC 610.

Protein Purification

The proteins, polypeptides and antigenic fragments of this invention can be purified by standard methods including, but not limited to, salt or alcohol precipitation, preparative disc-gel electrophoresis, isoelectric focusing, high pressure liquid chromatography (HPLC), reversed-phase HPLC, gel filtration, cation and anion exchange, partition chromatography and countercurrent distribution. Such purification methods are well known in the art and are disclosed, e.g., in *Guide to Protein Purification, Methods in Enzymology,* Vol. 182, M. Deutscher, Ed., 1990, Academic Press, New York, N.Y.

Purification steps can be followed by carrying out assays for ligand binding activity as described below. Particularly where a ligand is being isolated from a cellular or tissue source, it is preferable to include one or more inhibitors of proteolytic enzymes is the assay system, such as phenylmethanesulfonyl fluoride (PMSF).

Screening Systems and Methods

The present invention allows for the discovery of selective antagonists of the canine RANK ligand that may be useful in the treatment and management of a variety of diseases including inflammation, bone disease, osteoarthritis, rheumatoid arthritis, osteoporosis and pain. Thus, a ligand of the present invention can be employed in screening systems to identify antagonists of RANKL. Essentially, these systems provide methods for bringing together a RANK receptor, an appropriate ligand, including canine RANK ligand itself, and a sample to be tested for the presence of a canine RANKL antagonist.

Two basic types of screening systems can be used, a labeled-ligand binding assay and a "functional" assay. A labeled ligand for use in the binding assay can be obtained by labeling canine RANKL with a measurable group, as described below in connection with the labeling of antibodies. Various labeled forms of canine RANKL can be generated using standard techniques. Alternatively, the RANK receptor can be labeled.

Typically, a given amount of the RANK receptor is contacted with increasing amounts of a labeled ligand, such as labeled canine RANKL itself, and the amount of the bound labeled ligand is measured after removing unbound labeled ligand by washing. As the amount of the labeled ligand is increased, a point is eventually reached at which all RANK receptor binding sites are occupied or saturated. Specific receptor binding of the labeled ligand is abolished by a large excess of unlabeled ligand.

Preferably, an assay system is used in which non-specific binding of the labeled ligand to the RANK receptor is minimal. Non-specific binding is typically less than 50%, preferably less than 15%, and more preferably less than 10% of the total binding of the labeled ligand.

In principle, a binding assay of the present invention could be carried out using a soluble RANK receptor and the resulting receptor-labeled ligand complex could be precipitated, e.g., using an antibody against the ligand. The precipitate could then be washed and the amount of the bound labeled ligand could be measured.

Preferably, however, a RANK receptor is incorporated into the membrane of a cell. A membrane fraction can then be isolated from the cell and used as a source of the receptor for assay.

The binding assays of this invention can be used to identify antagonists of canine RANKL because they will interfere with the binding of the ligand to the RANK receptor.

In the basic binding assay, a method for identifying a canine RANKL antagonist comprises:

(a) contacting a RANK receptor or a subsequence thereof, in the presence of a known amount of canine RANKL with a sample to be tested for the presence of a canine RANKL antagonist; and (b) measuring the amount of canine RANKL bound to the receptor;

whereby a canine RANKL antagonist in the sample is identified by measuring substantially reduced binding of the RANKL to the RANK receptor, compared to what would be measured in the absence of such antagonist. As stated previously, either the RANKL or RANK may be labeled.

Determination of whether a particular molecule inhibiting binding of the canine RANK ligand to the RANK receptor is an antagonist or an agonist is then made in a second, functional assay. The functionality of molecules identified in the binding assay can be determined in cellular and animal models.

In cellular models, parameters for intracellular activities mediated by RANKL can be monitored. Such parameters include, but are not limited to, altered intracellular cAMP or $Ca^{2+}$ concentrations. Methods using animals or animal tissues for such activities can also be employed.

In the basic functional assay, a method for identifying an antagonist of a canine RANK ligand comprises:

(a) contacting cells expressing the canine RANKL polypeptide in the presence of a known amount of RANK or surrogate thereof with a sample to be tested for the presence of a canine RANK ligand antagonist; and (b) measuring at least one cellular function modulated by the binding of RANK to the polypeptide;

whereby a canine RANK ligand antagonist in the sample is identified by measuring substantially reduced effects on said cellular function compared to what would be measured in the absence of such antagonist.

Mammalian RANK Ligands from Other Species

The present invention provides methods for cloning RANK ligands from other species. Briefly, Southern and Northern blot analysis can be performed to identify cells from other species expressing genes encoding the RANK ligand. Complementary DNA (cDNA) libraries can be prepared by standard methods from mRNA isolated from such cells, and degenerate probes or PCR primers based on the nucleic acid and amino acid sequences provided herein can be used to identify clones encoding a RANK ligand.

Alternatively, expression cloning methodology can be used to identify particular clones encoding a RANK ligand. An antibody preparation which exhibits cross-reactivity with RANK ligands from a number of mammalian species may be useful in monitoring expression cloning.

However identified, clones encoding RANK ligand from various species can be isolated and sequenced, and the coding regions can be excised and inserted into an appropriate vector.

Localization of mRNA Encoding the Polypeptide of SEQ ID NO: 2

The present invention also provides compositions and methods for localization of messenger RNA coding for the polypeptide defined by the amino acid sequence of SEQ ID NO: 2.

Specifically, cell line blots containing approximately 2 μg of poly(A)$^+$ RNA per lane are purchased from Clontech (Palo Alto, Calif.). Probes are radiolabeled with [$\alpha^{32}$P] dATP, e.g., using the Amersham Rediprime random primer labeling kit (RPN1633). Prehybridization and hybridizations are performed at 65° C. in 0.5 M $Na_2HPO_4$, 7% SDS and 0.5 mM EDTA (pH 8.0). High stringency washes are conducted, e.g., at 65° C. with an initial wash in 6×SSC, 0.1% SDS for 15 min followed by two subsequent washes in 0.2×SSC, 0.1% SDS for 15 min. The mixture is then exposed at −70° C. to X-Ray film (Kodak) in the presence of intensifying screens. More detailed studies by cDNA library Southerns are performed with selected clones of nucleic acids having the nucleotide sequence defined by SEQ ID NO: 1 to examine their expression in other cell subsets.

Two prediction algorithms that take advantage of the patterns of conservation and variation in multiply aligned sequences, (Rost and Sander (1994) *Proteins* 19:55-72) and DSC (King and Stemberg (1996) *Protein Sci.* 5:2298-2310), are used.

Alternatively, two appropriate primers are selected and RT-PCR is used on an appropriate mRNA sample selected for the presence of message to produce a cDNA, e.g., a sample which expresses the gene.

Full length clones may be isolated by hybridization of cDNA libraries from appropriate tissues pre-selected by PCR signal.

Message for nucleic acids encoding a polypeptide having the amino acid sequence of SEQ ID NO: 2 are assayed by appropriate technology, e.g., PCR, immunoassay, hybridization or otherwise. Tissue and organ cDNA preparations are available, e.g., from Clontech, Mountain View, Calif.

Southern Analysis on cDNA libraries is performed as follows: DNA (5 μg) from a primary amplified cDNA library is digested with appropriate restriction enzymes to release the inserts, run on a 1% agarose gel and transferred to a nylon membrane (Schleicher and Schuell, Keene, N.H.).

Immunogenic Compositions. Vaccines, and Antibody Production

An "immunogenic composition" is a substance or a combination of substances, covalently or noncovalently combined, effective to elicit an immune response in an organism and/or from isolated immune system cells. An immune response is the reaction of the body to foreign substances, without implying a physiologic or pathologic consequence of such a reaction, i.e., without necessarily conferring protective immunity on the organism. An immune response may include one or more of the following: a cell mediated immune response, which involves the production of lymphocytes by the thymus in response to exposure to an antigen; and/or a humoral immune response, which involves production of plasma lymphocytes in response to antigen exposure with subsequent antibody production. Immunogenic compositions are useful as antigens to elicit the production of antibodies.

Antigenic (i.e., immunogenic) fragments of the canine RANK ligand of this invention, which may or may not have RANK receptor binding activity, may be produced as immunogens. Regardless of whether they bind RANK, such fragments, like the complete ligands, are useful as antigens for preparing antibodies, by standard methods, that can prevent binding to the receptors. Because it is well known in the art that epitopes generally contain at least about five, preferably at least about 8, amino acid residues [Ohno et al., *Proc. Natl. Acad. Sci.* USA 82:2945 (1985)], fragments used for the production of antibodies will generally be at least that size. Preferably, they will contain even more residues. Whether a given fragment is immunogenic can readily be determined by routine experimentation. Simply by way of example, preferred fragments of the canine RANKL polypeptide fragments include those listed by Table 1, supra.

The artisan will also appreciate that selection of desirable immunogenic fragments/epitopes of a polypeptide depends upon the tertiary structure of the polypeptide. Preferred fragments for eliciting binding antibodies are those peptide structures external to the folded polypeptide, e.g. peptide loops that comprise the outside or solvent-accessible portions of the folded structure and that are accessable to the immune system or immune cells. The polypeptide of SEQ ID NO: 2 primarily corresponds to the extracellular portion of the endogenous, cell-membrane bound canine RANKL. Based on murine RANKL tertiary structure and homologies within the TNF superfamily of proteins, Lam et al. [*J Clin Invest*, 108 (7):971-979 (2001), incorporated herein by reference] have reported, that the externally presented loops that are unique to murine RANKL are clustered in the solvent-accessible AA", CD, DE, and EF loops illustrated by FIG. 2 of the Lam et al. article (Id.). It is contemplated that the analogous regions of the canine RANKL of SEQ ID NO: 2 are preferred, but not exclusive, domains for antibody recognition and selective binding of the inventive canine RANKL polypeptide. Thus, canine RANKL polypeptides that are preferred as immunogens and/or as components of suitable fusion proteins and/or other vaccine preparations include, for example, a canine RANKL polypeptide fragment corresponding to the entire murine RANKL loop region, from about residue 110 to about residue 140 of SEQ ID NO:2, and well as the particular canine RANKL polypeptides listed by Table 2, below.

TABLE 2

From about residue 125 to about residue 160 of SEQ ID NO: 2;
From about residue 119 to about residue 153 of SEQ ID NO: 2;
From about residue 175 to about residue 200 of SEQ ID NO: 2;
From about residue 183 to about residue 192 of SEQ ID NO: 2;
From about residue 200 to about residue 225 of SEQ ID NO: 2;
From about residue 204 to about residue 211 of SEQ ID NO: 2;
From about residue 195 to about residue 215 of SEQ ID NO: 2;
From about residue 221 to about residue 227 of SEQ ID NO: 2;
as well as combinations of the foregoing.

Preferably, canine RANKL polypeptide and/or fragments, e.g., of Tables 1 and/or 2, are cross-linked to a carrier molecule to enhance their immunogenicity via a "carrier effect." Conjugation polypeptide and/or polypeptide fragments to an immunogenic carrier molecule renders them more immunogenic through what is commonly known as the "carrier effect". This is particularly preferred for extracellular polypeptides to which the treated mammal is typically immunologically tolerant.

Suitable carrier molecules include, e.g., proteins and natural or synthetic polymeric compounds such as polypeptides, polysaccharides, lipopolysaccharides, etc. Protein carrier molecules are especially preferred, including, but not limited to, keyhole limpet hemocyanin and mammalian serum proteins, such as human or bovine gamma-globulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the present invention can be coupled, e.g., using water-soluble carbodiimides, such as dicyclohexylcarbodiimide or glutaraldehyde. Coupling agents such as these can also be used to cross-link the fragments to themselves without the use of a separate carrier molecule. Such cross-linking into aggregates can also increase immunogenicity.

Immunogenicity can also be increased by the use of adjuvants, alone or in combination with coupling or aggregation. Suitable adjuvants for the vaccination of animals include, but are not limited to, Adjuvant 65 (containing peanut oil, mannide monooleate and aluminum monostearate); Freund's complete or incomplete adjuvant; mineral gels, such as aluminum hydroxide, aluminum phosphate and alum; surfactants, such as hexadecylamine, octadecylamine, lysolecithin, dimethyldioctadecylammonium bromide, N,N-dioctadecyl-N',N'-bis(2-hydroxymethyl) propanediamine, methoxyhexadecylglycerol and pluronic polyols; polyanions, such as pyran, dextran sulfate, poly IC, polyacrylic acid and carbopol; peptides, such as muramyl dipeptide, dimethylglycine and tuftsin; and oil emulsions. The polypeptides could also be administered following incorporation into liposomes or other microcarriers. Information concerning adjuvants and various aspects of immunoassays are disclosed, e.g., in the series by P. Tijssen, *Practice and Theory of Enzyme Immunoassays*, 3rd Edition, 1987, Elsevier, New York.

A vaccine (or vaccine composition) can be an antigen and/or a composition, including an immuogenic composition described above, and/or a formulation that when administered to a subject animal engenders an immunogenic challenge in a controlled manner in that subject animal. Vaccines of the present invention, for example, can comprise an antigen or an expressible nucleic acid (e.g., in a viral vector or naked DNA vector) that encodes an antigen. In a particular embodiment, the antigen is the canine RANKL polypeptide or an immunogenic fragment thereof. All of the forms of the canine RANKL polypeptide and immunogenic fragments thereof taught by the present invention may be part of such a vaccine. In a particular embodiment, administering a vaccine of the present invention to an animal subject serves to negate, at least in part, the biological action (activity) of the native RANKL of the subject animal. Vaccines of the present invention generally, but by no means always, comprise an adjuvant as exemplified above. Examples of methods of administering vaccines contemplated by the present invention include subcutaneous, parenteral, intraperitoneal, scarification, intravenous, intramuscular injection and infusion. The formulation, use and administration of vaccines are well known in the art and have been reviewed in published PCT application WO00/158071 and U.S. Pat. No. 6,645,500 B1, the contents of which are hereby incorporated by reference in their entireties.

The present invention also includes polyclonal and monoclonal (mAb) antibodies that bind to canine RANKL, and preferably antibodies that bind specifically to canine RANKL. As used herein, the term "antibody" refers to an immunoglobulin and/or fragments thereof. A naturally occurring immunoglbulin consists of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. An antibody or antibodies according to the present invention also encompass antibody fragments, i.e., antigen-binding fragments, for example, Fv, Fab, and F(ab')$_2$, engineered single-chain binding proteins, e.g., Huston et al., *Proc. Natl. Acad. Sci.U.S.A.*, 85, 5879-5883 (1988) and Bird et al., *Science*, 242,423426 (1988), incorporated herein by reference herein), as well as bifunctional hybrid antibodies (e.g., Lanzavecchia et al., *Eur. J. Immunol.* 17, 105 (1987)). See, generally, Hood et al., Immunology, Benjamin, N.Y., 2nd ed. (1984), Harlow and Lane, *Antibodies. A Laboratory Manual*, Cold Spring Harbor Laboratory (1988) and Hunkapiller and Hood, *Nature*, 323, 15-16 (1986), all of which are incorporated by reference herein.

For example, serum produced from animals immunized using standard methods can be used directly, or the IgG fraction can be separated from the serum using standard methods, such as plasmaphoresis or adsorption chromatography with IgG-specific adsorbents, such as immobilized Protein A. Alternatively, monoclonal antibodies can be prepared, and optionally, antigen binding fragments or recombinant binding proteins derived from such mAbs. Such MAbs or fragments thereof can be humanized by art-known methods if so desired.

Hybridomas producing mAbs that selectively bind canine RANKL of the present invention, or antigenic fragments of canine RANKL, are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., *Science* 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and, in general, involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay) or the like. Antibodies are recovered from the medium using standard protein purification techniques [Tijssen, *Practice and Theory of Enzyme Immunoassays* (Elsevier, Amsterdam, 1985)].

Many references are available to provide guidance in applying the above techniques [Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982)]. Monoclonal antibodies can also be produced using well-known phage library systems. See, e.g., Huse, et al., *Science* 246:1275 (1989); Ward, et al., *Nature*, 341:544 (1989).

Antibodies thus produced, whether polyclonal or monoclonal, can be used, e.g., in an immobilized form bound to a solid support by well known methods to purify the ligands by immunoaffinity chromatography.

Antibodies against the antigenic fragments can also be used, unlabeled or labeled by standard methods, as the basis for immunoassays of the canine RANK ligand. The particular label used will depend upon the type of immunoassay. Examples of labels that can be used include, but are not limited to, radiolabels, such as $^{32}P$, $^{125}I$, $^{3}H$ and $^{14}C$; fluorescent labels, such as fluorescein and its derivatives, rhodamine and its derivatives, dansyl and umbelliferone; chemiluminescers, such as luciferia and 2,3-dihydrophthalazinediones; and enzymes, such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, e.g., in *Immunoassay: A Practical Guide*, 1987, Chan (Ed.), Academic Press, Inc., Orlando, Fla. Such immunoassays could be carried out, for example, on fractions obtained during purification of the receptors.

The antibodies of the present invention can also be used to identify particular cDNA clones expressing canine RANKL in expression cloning systems.

Neutralizing antibodies specific for the ligand-binding site of a receptor can also be used as antagonists (inhibitors) to block RANKL binding. Such neutralizing antibodies can readily be identified through routine experimentation.

Antagonism of RANKL activity can be accomplished using complete antibody molecules, or well-known antigen binding fragments such as Fab, Fc, F(ab)$_2$, and Fv fragments. Definitions of such fragments can be found, e.g., in Klein, *Immunology* (John Wiley, New York, 1982); Parham, Chapter 14, in Weir, ed. *Immunochemistry*, 4th Ed. (Blackwell Scientific Publishers, Oxford, 1986). The use and generation of antibody fragments has also been described, e.g.: Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Plückthun [Bio/Technology 9:545 (1991)]. Alternatively, they can be chemically synthesized by standard methods.

The present invention also encompasses anti-idiotypic antibodies, both polyclonal and monoclonal, which are produced using the above-described antibodies as antigens. These antibodies are useful because they may mimic the structures of the ligands.

Pharmaceutical Compositions

The canine RANK ligand antagonists of this invention can be used therapeutically to block the activity of RANK ligand, and thereby to treat any medical condition caused or mediated by the RANK/RANKL system. The dosage regimen involved in a therapeutic application will be determined by the attending veterinarian, considering various factors which may modify the action of the therapeutic substance, e.g., the condition, body weight, sex and diet of the patient, time of administration and other clinical factors.

Typical protocols for the therapeutic administration of such substances are well known in the art. Administration of the pharmaceutical compositions of the present invention is typically by parenteral, intraperitoneal, intravenous, subcutaneous, intramuscular injection, infusion or any other acceptable systemic method. Often, treatment dosages are titrated upward from a low level to optimize safety and efficacy.

Dosages will be adjusted to account for the smaller molecular sizes and possibly decreased half-lives (clearance times) following administration. It will be appreciated by those skilled in the art, however, that the canine RANKL antagonists of the present invention encompass neutralizing antibodies or binding fragments thereof in addition to other types of inhibitors, including small organic molecules and inhibitory ligand analogs, which can be identified using the methods of the present invention.

An "effective amount" of a composition of the present invention is an amount that will ameliorate one or more of the well-known parameters that characterize medical conditions caused or mediated by RANKL.

Although the compositions of this invention could be administered in simple solution, they are more typically used in combination with other materials such as carriers, preferably pharmaceutical carriers. Useful pharmaceutical carriers can be any compatible, non-toxic substances suitable for delivering the compositions of the present invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g., *Remington's Pharmaceutical Science,* 17th Ed. (Mack Publishing Company, Easton, Pa., 1990). Alternatively, compositions of the present invention may be introduced into a patient's body by implantable drug delivery systems [Urquhart et al., *Ann. Rev. Pharmacol. Toxicol.* 24:199 (1984)].

Therapeutic formulations may be administered in many conventional dosage formulations. Formulations typically comprise at least one active ingredient, together with one or more pharmaceutically acceptable carriers. Formulations may include those suitable for oral, rectal, nasal or parenteral (including subcutaneous, intramuscular, intravenous and intradermal) administration.

The formulations may conveniently be presented in unit dosage form and may be prepared by any method well known in the art of pharmacy. See, e.g., Gilman et al. (eds.) (1990), *The Pharmacological Bases of Therapeutics,* 8th Ed., Pergamon Press; and *Remington's Pharmaceutical Sciences,* supra, Easton, Pa.; Avis et al. (eds.) (1993) *Pharmaceutical Dosage Forms: Parenteral Medications* Dekker, New York; Lieberman et al., (eds.) (1990) *Pharmaceutical Dosage Forms: Tablets* Dekker, New York; and Lieberman et al., (eds.) (1990), *Pharmaceutical Dosage Forms: Disperse Systems* Dekker, N.Y.

Anti-Sense Molecules

The present invention also encompasses anti-sense oligonucleotides capable of specifically hybridizing to mRNA encoding a canine RANK ligand having an amino acid sequence defined by SEQ ID NO: 2 or a subsequence thereof so as to prevent translation of the mRNA. Additionally, this invention contemplates anti-sense oligonucleotides capable of specifically hybridizing to the genomic DNA molecule encoding a canine RANKL having an amino acid sequence defined by SEQ ID NO: 2 or a subsequence thereof.

This invention further provides pharmaceutical compositions comprising (a) an amount of an oligonucleotide effective to reduce activity of canine RANKL by passing through a cell membrane and binding specifically with mRNA encoding canine RANKL in the cell so as to prevent its translation and (b) a pharmaceutically acceptable carrier capable of passing through a cell membrane. In an embodiment, the oligonucleotide is coupled to a substance that inactivates mRNA. In another embodiment, the substance that inactivates mRNA is a ribozyme.

The present invention may be better understood by reference to the following non-limiting examples, which are provided as exemplary of the invention. The following examples are presented in order to more fully illustrate embodiments of the present invention and should in no way be construed as limiting the broad scope of the present invention.

EXAMPLES

Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and General Methods

Some of the standard methods are described or referenced, e.g., in Maniatis, et al. (1982) Molecular Cloning, A Laboratory Manual, Cold Spring Harbor Laboratory, Cold Spring Harbor Press; Sambrook, et al., (1989) Molecular Cloning: A Laboratory Manual (2d ed.), vols. 1-3, CSH Press, NY; Ausubel, et al., Biology, Greene Publishing Associates, Brooklyn, N.Y.; or Ausubel, et al., (1987 and Supplements) Current Protocols in Molecular Biology, Greene and Wiley, New York; Innis, et al. (eds.)(1990) PCR Protocols: A Guide to Methods and Applications, Academic Press, N.Y.

Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in Methods in Enzymology vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, N.Y.; and Crowe, et al. (1992) OIAexpress: The High Level Expression & Protein Purification System QIAGEN, Inc., Chatsworth, Calif.

Cell culture techniques are described in Doyle, et al. (eds.) (1994) Cell and Tissue Culture: Laboratory Procedures, John Wiley and Sons, NY.

FACS analyses are described in Melamed, et al. (1990) Flow Cytometry and Sorting Wiley-Liss, Inc., New York, N.Y.; Shapiro (1988) Practical Flow Cytometry Liss, New York, N.Y.; and Robinson, et al. (1993) Handbook of Flow Cytometry Methods Wiley-Liss, New York, N.Y. Fluorescent labeling of appropriate reagents can be performed by standard methods.

Example 1

Cloning of Canine RANKL

Canine RANKL was cloned using a series of nested PCR strategies.

Nested PCR involves two sequential PCR reactions. Each PCR reaction generally contained 0.02 µg/µl of nucleic acid template, 1×PCR buffer, 0.8 mM dNTP's, 1.1 mM Mg(OAC)$_2$, 0.16 units/µl of rTth polymerase (recombinant thermostable Taq polymerase), 2 OD/ml of vector primer, and 0.2 OD/ml of gene specific primer. In the initial reaction, 30 cycles of PCR were performed using a vector specific primer and a gene specific primer (same or cross species primer). First, the reaction mixture was heated to 94° C. for 1 minute. The reaction mixture was then cycled 30 times; each cycle the reaction mixture being heated to 94° C. for 1 minute, then cooled to 65° C. for 5 minutes, followed by heating to 72° C. for 10 minutes. After completing 30 cycles, the reaction mixture remained at 72° C. for 10 minutes. Subsequently, a small aliquot of the PCR product of the first reaction served as the template for a second PCR reaction. The second PCR reaction used gene specific primers (same or cross species) that hybridized to sequences internal to or nested between the first set of primers. This is called double nesting. However, in some cases, the first reaction gene specific primer was used in the second set of reactions with a different gene specific primer (same or cross species) for a single nesting reaction. The second PCR reaction was cycled according to the same protocol as the first reaction.

A canine splenocyte activated cDNA library of primary DNA was prepared from canine splenocytes, with Concanavalin A (ConA) activiation, according to the method of Bolin et al., (1997), *The Journal of Neuroscience*, 17(14): 5493-5502, incorporated by reference here in its entirety. Briefly, splenocytes were obtained from fresh canine spleen by standard methods. RNA was isolated by standard techniques from separated canine splenocytes that were stimulated for 1, 2, 6, 12, and 24 hr with Concavalin A (Sigma, St. Louis, Mo.), interferon γ (γ-IFN) (200 U/ml) (Schering Plough, Kenilworth, N.J.), and anti-interleukin-10 (IL-10) antibody (10 µg/ml) (DNAX) and then pooled. Poly(A1) RNA was selected using oligotex beads (Qiagen, Chatsworth, Calif.). A cDNA library was constructed using this mRNA.

Nested PCR was performed using the GeneAmp XL PCR kit (Perkin Elmer, Branchburg, N.J.) on Canine Splenocyte activated cDNA library primary DNA. The library may either be purchased or constructed according to methods known in the art.

The first round PCR reaction mix contained the elements described above, with the vector specific primer being the T7 primer (SEQ ID NO: 3) and the gene specific primer being the Rank Ligand_Human/AS2 primer (SEQ ID NO: 4). The first round PCR reaction mixture was then cycled according to the procedure described above.

Two µl of the first round PCR product was used as a template for a second PCR reaction. The gene specific primers for the second reaction were the Rank Ligand_Human/S6 primer (SEQ ID NO: 5) and the Rank Ligand_Human/AS4 primer (SEQ ID NO: 6). The second reaction, containing materials as described above, was cycled as described above.

The above two rounds of PCR generated a 1.2 kb fragment. The fragment was extremely faint when subjected to agarose gel analysis. The 1.2 kb fragment was then cloned into the PCRII vector (Invitrogen, Carlsbad, Calif.). The screening of transformants did not yield a clone containing the 1.2 kb insert.

One µl of the above ligation mix (the 1.2 kb insert ligated to the PCRII vector) was then used as template for another PCR reaction. The primers used in this reaction were the Rank Ligand_Human/S3 primer (SEQ ID NO: 7) and the Rank Ligand_Human/AS4 primer (SEQ ID NO: 6). The reaction mixture was cycled 30 times according to the above described procedure. A 0.3 kb fragment was generated by this PCR reaction. The 0.3 kb fragment was then isolated by agarose gel electrophoresis and cloned into the PCRII vector. The sequence was confirmed by analysis to be an internal coding region of the canine RANK ligand. As is known in the art, T7 reads sense in both clones. These clones were called 01-7469A1 and 01-7469A2.

The above internal coding region of the canine RANK ligand was used to design canine specific PCR primers for subsequent nested PCR reactions. The goal was to isolate both upstream 5' and downstream 3' coding regions of the canine RANK ligand gene.

A 0.4 kb fragment of the 5' upstream coding region was generated using nested PCR. The first round reaction mixture included Canine Splenocyte activated cDNA library primary DNA as a template, and the T7 primer (SEQ ID NO: 3) and the Rank Ligand_Dog/AS1 primer (SEQ ID NO: 8). The second round reaction mixture included 2 µl of the first round reaction product as a template with Rank Ligand_Human/S6 primer (SEQ ID NO: 5) and Rank Ligand_Dog/AS2 primer (SEQ ID NO: 9). Both rounds of PCR were cycled according to the above protocol. The resulting sequence was confirmed by sequence analysis to be canine RANK ligand, excluding the 21 bp contributed by the Human primer Rank Ligand_Human/S6. This clone was called 01-7557B10.

A 1.3 kb fragment of the 3' coding region with UTR was generated using nested PCR. The first round reaction mixture included Canine Splenocyte activated cDNA library primary DNA as a template, and the Rank Ligand_Dog/S1 primer (SEQ ID NO: 10) and the vector specific primer Sp6 (SEQ ID NO: 11). The second round reaction mixture included 2 µl of first round reaction product as a template with Rank Ligand-Dog/S2 primer (SEQ ID NO: 12) and vector specific primer pSPORT1 (SEQ ID NO: 13). The resulting PCR product was confirmed by sequence analysis to be canine RANK ligand. This clone was called 01-7557A5.

The 1.3 kb sequence of 3' coding region with UTR allowed for two gene specific canine RANK ligand primers, Rank Ligand-Dog/AS4 (SEQ ID NO: 14) and Rank Ligand_Dog/AS3 (SEQ ID NO: 15), to be designed in the 3' UTR which made it possible to construct a nearly intact canine RANK ligand gene that could be used for protein expression.

One final nested PCR strategy was performed. The first round reaction mixture included T7 primer (SEQ ID NO: 3) and Rank Ligand_Dog/AS3 primer (SEQ ID NO: 15). The second round reaction mixture included 2 µl of the first round reaction product as a template with Rank Ligand_Human/S6 primer (SEQ ID NO: 5) and Rank Ligand_Dog/AS4 primer (SEQ ID NO: 14). The resulting product was a 0.989 kb fragment. The 0.989 kb fragment was cloned into the PCRII vector and confirmed by sequence analysis to be canine RANK ligand, excluding the 21 bp contributed by the Human primer Rank Ligand_Human/S6 (SEQ ID NO: 5). This clone was called 02-8136A5.

Example 2

Expression and Purification of Canine RANKL

Standard molecular biology techniques are used to make a chimeric DNA construct encoding, sequentially, residues 1-15 of the preprotrypsin signal peptide, the FLAG™ sequence DYKDDDD (SEQ ID NO: 16),KL (encoding a HindIII site used in construction), residues VA, residues 155-319 of the ectodomain from canine RANKL, residues PRPPTPGNL (SEQ ID NO: 17),encoding a proteolytic cleavage site), and residues 99-330 from the constant region of human IgG gamma 1. This chimeric coding region is inserted into a modified pQB1-AdCMV5-GFP adenovirus transfer vector (Quantum Biotechnologies, Montreal, Canada) and used to make recombinant adenovirus, as previously described by Hoek et al., "Down-regulation of the macrophage lineage through interaction with OX2", *Science*, vol. 290, pp. 1768-1771 (Dec. 1, 2000). Control adenovirus encodes the same chimeric construct minus the canine RANKL ectodomain. Recombinant Ig fusion proteins are prepared using methods previously described in Oppmann et al., "Novel p19 protein engages IL-12p40 to form a cytokine, IL-23, with biological activities similar as well as distinct from IL-12", *Immunity*, vol. 13, pp. 715-25 (November 2000).

It should be noted that other expression configurations can also be engineered and would be expected to result in a functional protein. For example, the Ig domain could be placed between the FLAG™ sequence and the RANKL sequence. Purification could be via the identical method.

Example 3

Isolation of Homologous RANKL Genes

The canine RANKL cDNA can be used as a hybridization probe to screen a library from a desired source, e.g., a primate cell cDNA library. Many different species can be screened both for stringency necessary for easy hybridization, and for presence using a probe. Appropriate hybridization conditions can be used to select for clones exhibiting specificity of cross hybridization.

Screening by hybridization or PCR using degenerate probes based upon the peptide sequences can also allow isolation of appropriate clones. Alternatively, use of appropriate primers for PCR screening can yield enrichment of appropriate nucleic acid clones.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against canine RANKL can be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) Current Protocols in Immunology Wiley/Greene; and Harlow and Lane (1989) Antibodies: A Laboratory Manual Cold Spring Harbor Press. The resulting antibodies are used, e.g., for screening, panning, or sorting.

Example 4

Preparation of Rat Anti-Canine RANKL mAb

Rat anti-canine RANKL mAbs are produced from splenocytes of an 8 week old female Lewis rat (Harlan Sprague-Dawley, Indianapolis, Ind.) immunized with canine RANKL.Ig fusion protein. The rat is primed i.p. with 25 µg of fusion protein in complete Freund's adjuvant and subsequently boosted three times i.p. with 10 µg (day 25), 5 µg (day 40) and 10 µg (day 54) in incomplete Freund's adjuvant, respectively. The final boosts are performed both i.v. and i.p. at day 83 with 10 µg of fusion protein in saline solution and incomplete Freund's adjuvant, respectively. Splenocytes are fused at day 87 with mouse myeloma P3X63-AG8.653 using PEG 1500 (Roche Diagnostics, Mannheim, Germany). Hybridoma supernatants are screened by indirect ELISA, on both the fusion and control Ig protein, to identify specific mAb-producing hybridomas. These are further characterized by methods such as Western blot, immuno-precipitation and FACS analysis (e.g., on canine activated T cells). Selected positive hybridoma lines are subcloned and grown in serum free medium supplemented with SITE (Sigma, St. Louis, Mo.). Antibodies are purified via HiTrap SP and Q columns (Amersham Pharmacia Biotech), and screened for their ability to inhibit RANKL-induced biological responses such as activation of NF-κB or activation of osteoclasts using, e.g., the OCL formation assay described by Yasuda et al., Osteoclast differentiation factor is a ligand for osteoprotegerin/osteoclastogenesis-inhibitory factor and is identical to TRANCE/RANKL, *Proc. Natl. Acad. Sci.*, vol. 95, pp. 3597-3602 (1998).

Many modifications and variations of this invention can be made without departing from its spirit and scope, as will be apparent to those skilled in the art. The specific embodiments described herein are offered by way of example only, and the present invention is to be limited only by the terms of the appended claims, together with the full scope of equivalents to which such claims are entitled. Numerous references are cited in the specification, the disclosures of which are incorporated by reference in their entireties.

What is claimed is:

1. An isolated nucleic acid molecule encoding a polypeptide comprising the amino acid sequence of SEQ ID NO:2.

2. The isolated nucleic acid molecule of claim 1 that comprises the nucleotide sequence of SEQ ID NO:1.

3. A replicable nucleic acid vector comprising the nucleic acid molecule of claim 2.

4. A host cell comprising the replicable nucleic acid vector of claim 3.

5. A nucleic acid molecule that is a complement to said isolated nucleic acid molecule of claim 1; wherein said complement is the complementary strand to said isolated nucleic acid molecule.

6. The isolated nucleic acid molecule of claim 1 that is DNA or RNA.

7. A replicable nucleic acid vector comprising the nucleic acid molecule of claim 1.

8. A host cell comprising the replicable nucleic acid vector of claim 7.

9. A polynucleotide that hybridizes under stringent conditions to the complement of an isolated nucleic acid molecule encoding a polypeptide comprising the amino acid sequence of SEQ ID NO:2; provided that said polynucleotide does not encode a human, a murine, or a rat receptor activator of NF-κB ligand polypeptide; wherein said stringent conditions include a hybridization temperature at 65° C., in 0.5M Na$_2$HPO$_4$, 7% SDS, and 0.5 mM EDTA, pH 8.0, and washes at 65° C., with an initial wash in 6×SSC, 0.1% SDS, for 15 minutes, followed by two subsequent washes in 0.2×SSC, 0.1% SDS for 15 minutes.

10. A replicable nucleic acid vector comprising the nucleic acid molecule of claim 9.

11. A host cell comprising the replicable nucleic acid vector of claim 10.

12. An isolated nucleic acid molecule comprising an open reading frame encoding an immunogenic fusion protein comprising a canine receptor activator of the NF-κB ligand comprising the amino acid sequence of SEQ ID NO:2 joined to one or more additional peptide domains.

13. The nucleic acid molecule of claim 12 that is RNA or DNA.

14. A replicable nucleic acid vector comprising the nucleic acid molecule of claim 12.

15. The replicable nucleic vector of claim 14 selected from the group consisting of a plasmid, a phage, a cosmid, a mini-chromosome, and a virus.

16. The replicable nucleic vector of claim 14 that is suitable for expression of the vector by a eukaryotic host cell, a prokaryotic host cell, or both.

17. The replicable nucleic vector of claim 14, comprising a suitable promoter operably linked 5' to the open reading frame encoding said immunogenic fusion protein.

18. The replicable nucleic vector of claim 17 that comprises an operably linked nucleic acid sequence encoding a leader peptide enabling secretion or membrane integration of said immunogenic fusion protein.

19. A host cell comprising the replicable nucleic acid vector of claim 14.

20. The host cell of claim 19 that is a microorganism selected from the group consisting of a bacterium, a yeast, and a protozoan.

21. The host cell of claim 19 that is derived from a multicellular organism selected from a fungus, an insect cell, a plant cell, and a mammalian cell.

22. A method of producing an immunogenic fusion protein comprising culturing the host cell of claim 19 under conditions suitable for expressing said immunogenic fusion protein.

* * * * *

SEQUENCE LISTING

<160> NUMBER OF SEQ ID NOS: 15

<210> SEQ ID NO 1
<211> LENGTH: 989
<212> TYPE: DNA

<210> SEQ ID NO 1
<211> LENGTH: 989
<212> TYPE: DNA
<213> ORGANISM: Artificial Sequence
<220> FEATURE:
<223> OTHER INFORMATION: artificial sequence for canine RANK ligand
<220> FEATURE:
<221> NAME/KEY: misc_feature
<222> LOCATION: (1)..(21)
<223> OTHER INFORMATION: human primer sequence
<220> FEATURE:
<221> NAME/KEY: misc_feature
<222> LOCATION: (865)..(867)
<223> OTHER INFORMATION: stop codon

<400> SEQUENCE: 1

```
ccatgcgccg cgccagcaga gactacagca agtacctgcg ccgcctcccg ctccgtggcc      60
gtggccttcc tggggctggg gctgggccag gtggtctgca gcgtcgccct gttcctctac     120
ttcagggctc agatggatcc taatagaata tcagaagatg acactcactg cattaataga     180
attttcaaac tccatgaaaa tgcagatttg caagacacaa ctctggagaa tcaagacaca     240
aaattaatac ctgattcgtg taagagcatt aagcaggcct tccgagccgc cgtacaaaag     300
gaattacaac atattgttag atcacaacac atcagagcag aaaaagctat gatggaaggt     360
tcatggttgg aaatggccag gaggggcaag actcatactc aaccttttgc tcatctcact     420
atcaatgcca ctgacatccc atctggttcc cacaaagtga gtctgtcctc ctggtaccat     480
gaccgaggtt gggccaagat ctccaacatg actttcagca atgggaaact aatagttaac     540
caagatggct tttatttcct gtacgccaac atttgcttta gacatcatga acttcagga     600
gacctcgcca cagagtatct tcagctgatg gtgtatgtca ctaaaaccag catcaaaatc     660
ccgagttctc atacactgat gaaaggaggt agcaccaaat actggtcagg gaattctgaa     720
ttccattttt attccataaa cgttggagga tttttaagc tacgatctgg tgaggaaata     780
agcatcgagg tatccaaccc atcactactg gacccagatc aagatgcaac atactttggg     840
gcttttaagg ttctagatat agattgagtc ccatttatg gagtgttatt ctgtatttcc     900
gaggatgtat ggaaaatttt tttaaacaag gcaagaaaga tgtatataga gtgagacta     960
ctaaggggta tgacccacaa tgatacaag                                       989
```

<210> SEQ ID NO 2
<211> LENGTH: 275
<212> TYPE: PRT
<213> ORGANISM: Artificial Sequence
<220> FEATURE:
<223> OTHER INFORMATION: artificial sequence for canine RANK ligand

<400> SEQUENCE: 2

```
Ala Ala Ser Arg Ser Val Ala Val Ala Phe Leu Gly Leu Gly Leu Gly
1               5                   10                  15

Gln Val Val Cys Ser Val Ala Leu Phe Leu Tyr Phe Arg Ala Gln Met
            20                  25                  30

Asp Pro Asn Arg Ile Ser Glu Asp Asp Thr His Cys Ile Asn Arg Ile
        35                  40                  45

Phe Lys Leu His Glu Asn Ala Asp Leu Gln Asp Thr Thr Leu Glu Asn
    50                  55                  60

Gln Asp Thr Lys Leu Ile Pro Asp Ser Cys Lys Ser Ile Lys Gln Ala
65                  70                  75                  80

Phe Arg Ala Ala Val Gln Lys Glu Leu Gln His Ile Val Arg Ser Gln
                85                  90                  95

His Ile Arg Ala Glu Lys Ala Met Met Glu Gly Ser Trp Leu Glu Met
            100                 105                 110
```

```
Ala Arg Arg Gly Lys Thr His Thr Gln Pro Phe Ala His Leu Thr Ile
        115                 120                 125

Asn Ala Thr Asp Ile Pro Ser Gly Ser His Lys Val Ser Leu Ser Ser
        130                 135                 140

Trp Tyr His Asp Arg Gly Trp Ala Lys Ile Ser Asn Met Thr Phe Ser
145                 150                 155                 160

Asn Gly Lys Leu Ile Val Asn Gln Asp Gly Phe Tyr Phe Leu Tyr Ala
                165                 170                 175

Asn Ile Cys Phe Arg His His Glu Thr Ser Gly Asp Leu Ala Thr Glu
                180                 185                 190

Tyr Leu Gln Leu Met Val Tyr Val Thr Lys Thr Ser Ile Lys Ile Pro
            195                 200                 205

Ser Ser His Thr Leu Met Lys Gly Gly Ser Thr Lys Tyr Trp Ser Gly
        210                 215                 220

Asn Ser Glu Phe His Phe Tyr Ser Ile Asn Val Gly Gly Phe Phe Lys
225                 230                 235                 240

Leu Arg Ser Gly Glu Glu Ile Ser Ile Glu Val Ser Asn Pro Ser Leu
                245                 250                 255

Leu Asp Pro Asp Gln Asp Ala Thr Tyr Phe Gly Ala Phe Lys Val Leu
                260                 265                 270

Asp Ile Asp
        275

<210> SEQ ID NO 3
<211> LENGTH: 18
<212> TYPE: DNA
<213> ORGANISM: Artificial Sequence
<220> FEATURE:
<223> OTHER INFORMATION: T7 primer

<400> SEQUENCE: 3
taatacgact cactatag                                                18

<210> SEQ ID NO 4
<211> LENGTH: 21
<212> TYPE: DNA
<213> ORGANISM: Artificial Sequence
<220> FEATURE:
<223> OTHER INFORMATION: RANKL human/AS2 primer

<400> SEQUENCE: 4
ggtgtgtgag actactaaga g                                            21

<210> SEQ ID NO 5
<211> LENGTH: 21
<212> TYPE: DNA
<213> ORGANISM: Artificial Sequence
<220> FEATURE:
<223> OTHER INFORMATION: RANKL human/S6 primer

<400> SEQUENCE: 5
ccatgcgccg cgccagcaga g                                            21

<210> SEQ ID NO 6
<211> LENGTH: 20
<212> TYPE: DNA
<213> ORGANISM: Artificial Sequence
<220> FEATURE:
<223> OTHER INFORMATION: RANKL human/AS4 primer

<400> SEQUENCE: 6
```
gccaagatct ccaacatgac                                              20

<210> SEQ ID NO 7
<211> LENGTH: 22
<212> TYPE: DNA
<213> ORGANISM: Artificial Sequence
<220> FEATURE:
<223> OTHER INFORMATION: RANKL human/S3 primer

<400> SEQUENCE: 7
gacacaactc tggagagtca ag                                           22

<210> SEQ ID NO 8
<211> LENGTH: 24
<212> TYPE: DNA
<213> ORGANISM: Artificial Sequence
<220> FEATURE:
<223> OTHER INFORMATION: RANKL dog/AS1 primer

<400> SEQUENCE: 8
gccactgaca tcccatctgg ttcc                                         24

<210> SEQ ID NO 9
<211> LENGTH: 24
<212> TYPE: DNA
<213> ORGANISM: Artificial Sequence
<220> FEATURE:
<223> OTHER INFORMATION: RANKL dog/AS2 primer

<400> SEQUENCE: 9
ccaaccatga accttccatc atag                                         24

<210> SEQ ID NO 10
<211> LENGTH: 24
<212> TYPE: DNA
<213> ORGANISM: Artificial Sequence
<220> FEATURE:
<223> OTHER INFORMATION: RANKL dog/S1 primer

<400> SEQUENCE: 10
ctatgatgga aggttcatgg ttgg                                         24

<210> SEQ ID NO 11
<211> LENGTH: 18
<212> TYPE: DNA
<213> ORGANISM: Artificial Sequence
<220> FEATURE:
<223> OTHER INFORMATION: Sp6 primer

<400> SEQUENCE: 11
atttaggtga cactatag                                                18

<210> SEQ ID NO 12
<211> LENGTH: 24
<212> TYPE: DNA
<213> ORGANISM: Artificial Sequence
<220> FEATURE:
<223> OTHER INFORMATION: RANKL dog/S2 primer

<400> SEQUENCE: 12
gccactgaca tcccatctgg ttcc                                         24

<210> SEQ ID NO 13
<211> LENGTH: 20
<212> TYPE: DNA
<213> ORGANISM: Artificial Sequence -continued

```
<220> FEATURE:
<223> OTHER INFORMATION: pSPORT1 primer

<400> SEQUENCE: 13
gtacgtaagc ttggatcctc                                               20

<210> SEQ ID NO 14
<211> LENGTH: 23
<212> TYPE: DNA
<213> ORGANISM: Artificial Sequence
<220> FEATURE:
<223> OTHER INFORMATION: RANKL dog/AS4 primer

<400> SEQUENCE: 14
cttgtatcat tgtgggtcat acc                                           23

<210> SEQ ID NO 15
<211> LENGTH: 24
<212> TYPE: DNA
<213> ORGANISM: Artificial Sequence
<220> FEATURE:
<223> OTHER INFORMATION: RANKL dog/AS3 primer

<400> SEQUENCE: 15
ccagattaga gcaattatgg ttgc                                          24
```